(12) United States Patent
Hölzemann et al.

(10) Patent No.: US 6,576,637 B1
(45) Date of Patent: Jun. 10, 2003

(54) β-ALANINE DERIVATIVES

(75) Inventors: Günter Hölzemann, Seeheim-Jugenheim (DE); Simon Goodmann, Darmstadt (DE); Alfred Jonczyk, Darmstadt (DE); Wolfgang Stähle, Ingelheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 09/913,933

(22) PCT Filed: Feb. 8, 2000

(86) PCT No.: PCT/EP00/00969

§ 371 (c)(1),
(2), (4) Date: Aug. 20, 2001

(87) PCT Pub. No.: WO00/48996

PCT Pub. Date: Aug. 24, 2000

(30) Foreign Application Priority Data

Feb. 20, 1999 (DE) .......................................... 199 07 370
Dec. 1, 1999 (DE) .......................................... 199 57 787

(51) Int. Cl.$^7$ ...................... C07D 213/74; A61K 31/44; A61K 31/4402
(52) U.S. Cl. ........................ 514/275; 514/352; 544/330; 544/332; 546/304; 546/309
(58) Field of Search ................................ 546/304, 309; 544/330, 332; 514/275, 352

(56) References Cited

FOREIGN PATENT DOCUMENTS

| GB | 2327609 A | 2/1999 |
|----|-----------|--------|
| WO | WO 9724124 A | 7/1997 |
| WO | WO9726250 A | 7/1997 |

OTHER PUBLICATIONS

Neunhoeffer et al., Chemistry of 1,2,3–Triazines And 1,2, 4–Triazines, Tetrazines, And Pentazines, pp. 1296–1299, 1978.*
Kim et al., Vitronectin–driven Human Keratinocyte Locomotion is Mediated by the alphavbeta5 Integrin Receptor, J. Biol. Chem., vol. 269, No. 43, pp. 26926–26932, Oct. 1994.*
Schvartz et al., Molecules in focus Vitronectin, The Int. J. of Biochem. & Cell Biology, vol. 31, pp. 539–544, 1999.*
Douglas, Jr. et al., Introduction of Viral Diseases, Cecil Textbook of Medicine, 20th Edition, vol. 2, pp. 1739–1747, 1996.*
Roivainen et al., Entry of Coxsackievirus A9 into Host Cells: Specific Interactions with alphavbeta3 Integrin, the Vitronectin Receptor, Virology, vol. 203, pp. 357–365, 1994.*
Agrez et al., Integrin alphavbeta6 Coxsackievirus B1 Lytic Infection of Human Colon Cancer Cells, Virology, vol. 239, pp. 71–77, 1997.*
Simone, Oncology: Introduction, Cecil Textbook of Medicine, 20th Edition, vol. 1, pp. 1004–1010, 1996.*
Agrez et al., The alphavbeta6 Integrin Induces Gelatinase B Secretion in Colon Cancer Cells, Int. J. Cancer, vol. 81, pp. 90–97, 1999.*
Gladson et al., Vitronectin Expression in Differentiating Neuroblastic Tumors, Am. J. of Pathology, vol. 150, No. 5, pp. 1631–1646, May 1997.*
Nip et al., The role of the integrin vitronectin receptor alphavbeta3 in melanoma metastasis, Cancer and Metastasis Reviews, vol. 14, pp. 241–252, 1995.*
Brooks, Integrin alphavbeta3: A Therapeutic Target, DN & P, 10(8), pp. 456–461, Oct. 1997.*

* cited by examiner

Primary Examiner—Deepak Rao
(74) Attorney, Agent, or Firm—Millen, White, Zelano & Branigan, P.C.

(57) ABSTRACT

The invention relates to β-alanine derivatives of formula (I), wherein $Q_1$, $Q_2$, $Q_3$, $Q_4$, $R_1$, $R_2$, $R_3$, $R_4$, $R_5$, $R_6$ and n have the meaning as disclosed in the disclosure, and to their physiologically acceptable salts or solvates. Said substances are integrin inhibitors and can be used in the treatment of thrombosis, heart infarct, coronary heart diseases, arteriosclerosis, inflammations, tumors, osteoporosis, infections and restenosis after angioplasty or in pathological processes induced or propagated by angiogenesis.

10 Claims, No Drawings

β-ALANINE DERIVATIVES

The invention relates to β-alanine derivatives of the formula I

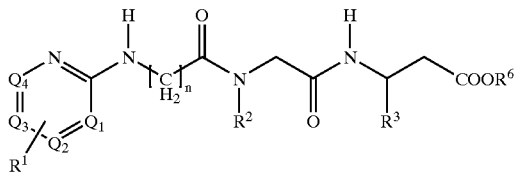

in which $Q_1$, $Q_2$, $Q_3$ or $Q_4$ is, in each case, independently of one another, CH or N, $R^1$ is H, A, Ar, Hal, OH, OA, $CF_3$ or $OCF_3$, $R^2$ is H or A, $R^3$ is,

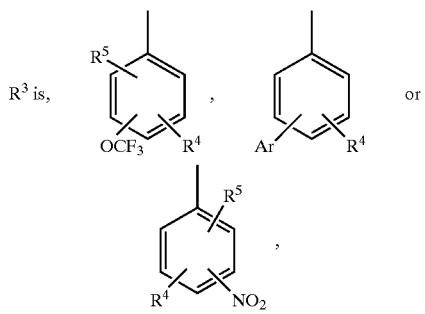

$R^4$ and $R^5$ are, in each case independently of one another H, A, Hal, OH, OA, $CF_3$, $OCF_3$, CN, $NH_2$, NHA, $NA_2$ or NH—C (O) A, $R^6$ is H, A, —$(CH_2)_m$—OH, —$(CH_2)_m$—O—C (O) A or —$(CH_2)_m$—Ar, A is alkyl with 1 to 6 C atoms, Ar is unsubstituted or mono-, di- or trisubstituted aryl, Hal is F, Cl, Br or I, n is 2, 3, 4, 5 or 6, m is 1, 2, 3 or 4, and their physiologically acceptable salts and solvates.

Partly similar compounds are disclosed in WO 97/26250 or WO 97/24124.

The invention was based on the object of finding novel compounds with valuable properties, in particular those which can be used to produce pharmaceuticals.

It has been found that the compounds of the formula I and their salts have very valuable pharmacological properties while being well tolerated. In particular, they act as integrin inhibitors, in particular inhibiting the interactions with the αvβ3 or αvβ5 integrin receptors with ligands such as, for example, the binding of vitronectin to the αvβ3 integrin receptor. Integrins are membrane-bound, heterodimeric glycoproteins which consist of an α subunit and of a smaller. β subunit. The relative affinity and specificity for ligand binding is determined by the combination of the various α and β subunits. The compounds according to the invention show particular activity in the case of the integrins αvβ1, and αvβ3, αvβ5, αIIbβ3, and αvβ6 and αvβ8, preferably of αvβ3 and αvβ5. In particular, potent selective inhibitors of the integrin αvβ3 have been found. The αvβ3 integrin is expressed on a number of cells, for example endothelial cells, smooth vascular muscle cells, for example of the aorta, cells for breaking down bone matrix (osteoclasts) or tumour cells.

The effect of the compounds according to the invention can be detected, for example, by the method described by J. W. Smith et al., in J. Biol. Chem. 1990, 265, 12267–12271. The dependence of the development of angiogenesis on the interaction between vascular integrins and extracellular matrix proteins is described by P. C. Brooks, R. A. Clark, and D. A. Cheresh in Science 1994, 264, 569–571.

The possibility of inhibiting this interaction and thus for inducing apoptosis (programmed cell death) of angiogenic vascular cells by a cyclic peptide is described by P. C. Brooks, A. M. Montgomery, M. Rosenfeld, R. A. Reisfield, T. Hu, G. Klier and D. A. Cheresh in Cell 1994, 79, 1157–1164. Descriptions are given therein of, for example, αvβ3 antagonists or antibodies against αvβ3 which bring about shrinkage of tumours through induction of apoptosis.

The experimental demonstration that the compounds according to the invention also prevent adhesion of living cells to the appropriate matrix proteins, and accordingly, also prevent the adhesion of tumour cells to matrix proteins can be provided in a cell adhesion test in analogy to the method of F. Mitjans et al., Cell Science 1995, 108, 2825–2838.

The compounds of the formula I are able to inhibit the binding of metalloproteinases to integrins and thus prevent the cells being able to utilize the enzymatic activity of the proteinase. One example is to be found in the ability to inhibit the binding of MMP-2 (matrix metalloproteinase 2) to the vitronectin receptor $α_vβ_3$ by a cylcic RGD peptide, as described in P. C. Brooks et al., Cell 1996, 85, 683–693.

Compounds of the formula I which block the interaction of integrin receptors and ligands such as, for example, of fibrinogen on the fibrinogen receptor (glycoprotein IIb/IIIa) prevent, as antagonists, the spread of tumour cells by metastasis and can therefore be employed as substances with antimetastatic activity in operations in which the tumours are surgically removed of dealt with. This is demonstrated by the following observations:

The spread of tumour cells from a local tumour into the vascular system takes place by the formation of microaggregates (microthrombi) through the interaction of the tumour cells with blood platelets. The tumour cells are shielded by the protection in the microaggregate and are not recognized by the cells of the immune system. The microaggregates are able to attach to vessel walls, which facilitates further penetration of tumour cells into the tissue. Since the formation of microthrombi is mediated by a ligand binding to the corresponding integrin receptors, for example αvβ3 or αIIbβ3, on activated blood platelets, the appropriate antagonists can be regarded as effective metastasis inhibitors.

The compounds of formula I can be employed as active pharmaceutical ingredients in human and veterinary medicine, in particular for the prophylaxis and/or therapy of circulatory disorders, thrombosis, myocardial infarct, arteriosclerosis, stroke, angina pectoris, tumorous disorders such as tumour development or tumour metastasis, osteolytic diseases such as osteoporosis, diseases with pathological angiogenesis, such as, for example, inflammations, ophthalmological diseases, diabetic retinopathy, macular degeneration, myopia, ocular histoplasmosis, rheumatoid arthritis, osteoarthritis, rubeotic glaucoma, ulcerative colitis, Crohn's disease, atherosclerosis, psoriasis, restenosis after angioplasty, multiple sclerosis, viral infection, bacterial infection, fungal infection, in acute kidney failure and in wound healing to assist the healing process.

The compounds of the formula I can be employed as substances with antimicrobial activity in operations where biomaterials, implants, catheters or heart pacemakers are used.

They moreover have an antiseptic effect. The antimicrobial activity can be demonstrated by the method described by P. Valentin-Weigund et al. in Infection and Immunity, 1988, 2851–2855.

Selected compounds of the formula I are, in particular, selective $\alpha\upsilon\beta3$ and $\alpha\upsilon\beta6$ integrin receptor inhibitors.

Selected compounds of the formula I are, in particular, selective $\alpha\upsilon\beta5$ and $\alpha\upsilon\beta6$ integrin receptor inhibitors. Selected compounds of the formula I are, in particular, selective $\alpha\upsilon\beta3$ and $\alpha\upsilon\beta5$ and $\alpha\upsilon\beta5$ integrin receptor inhibitors.

The effect of a compound on an $\alpha\upsilon\beta5$ integrin receptor and thus the activity as inhibitor can be demonstrated, for example, by the method described by J. W. Smith et al. in J. Biol. Chem. 1990, 265, 12267–12271. The effect of a compound on an $\alpha\upsilon\eta6$ integrin receptor and thus the activity as inhibitor can be demonstrated, for example, by the method described by J. W. Smith et al. in J. Biol. Chem. 1990, 265, 12267–12271.

These selected compounds are particularly suitable for therapy or for controlling pathological processes which can be influenced by the integrins $\alpha\upsilon\beta3$ and/or $\alpha\upsilon\beta5$ and $\alpha\upsilon\beta6$. Examples of angiogenic pathologies are skin disorders such as psoriasis, bullous pemphigus, dermatitis and erythemas, as well as pulmonary fibrosis, cystic fibrosis, endometriosis, cirrhosis or the liver of periodontitis, and they can be influenced through $\alpha\upsilon\beta3$ and/or $\alpha\upsilon\beta5$ inhibitors, and pathologies of epithelial cells which can be influenced through $\alpha\mu\beta6$ inhibitors are, in particular, carcinomas and the abovementioned skin disorders and pulmonary fibrosis (Lit.: Healy D. L. et al., Hum. Reprod. Update 1998, 4 (5), 736–40; Creamer D. et al., Br. J. Dermatol. 1997, 137, 851–5; Norrby K., APMIS, 1997, 105, 417–37; Creamer D. et al., Br. J. Dermatol. 1997, 136, 859–65; Polverini P. J., Crit. Rev. Oral. Biol. Med, 1995, 6, 230–47; Brown L. F. et al., J. Invest. Dermatol. 1995, 104, 744–9; Hoyt D. G. et al., Am. J. Physiol., 1997, 273, L612–7; Pilewski J. M. et al., ibid 1997, 273, L256–63 or Goldman M. et al., Gene. Ther. 1996, 3, 811–8).

A preferred use of these selected compounds is in cancer therapy.

Approaches to solutions for cancer therapy usually concentrate on controlling a part-region, a compartment, in the development of a solid tumour. Compartments are, inter alia, the development of the tumour per se or the blood vessels growing into the tumour, which are responsible for the supply of nutrients to the tumour. As soon as the supply of nutrients to the tumour is restricted, the production and secretion of polypeptide growth factors are induced by transcriptional activators, usually via hypoxic or hypoglycaemic promoters. These factors activate the sprouting of blood vessels. In order for the endothelial cells of the blood vessel to be able to divide, anti-apoptotic signals are necessary and are released by cell surface receptors and the integrin family. The integrin receptors $\alpha\upsilon\beta3$ and $\alpha\upsilon\beta5$ are particularly responsible for this release (Lit.: P. C. Brooks, Eur. J. Cancer, 1996, 32A, 2423–2429; P. C. Brooks et al., Cell, 1994, 79, 1157–1164).

Inhibitions of these integrin receptors $\alpha\upsilon\beta3$ and/or $\alpha\upsilon\beta5$, in particular of $\alpha\upsilon\beta3$, induces apoptosis of the activated endothelial cells of the blood vessel growing into the tumour, while the normal vascular bed, which is at rest, remains in tact. The tumour loses its supply of nutrients, and thus its development is stopped. The tumour per se, that is to say the degenerate cancer cells are, however, not impaired by this therapeutic approach, so that growth of the tumour can start again after the treatment ceases.

The integrin receptors on the surface of tumour cells differ significantly from those expressed on normal tissue. For example, high de novo expression of the rare integrin $\alpha\upsilon\beta6$ is found on many carcinomas, whereas $\alpha\upsilon\beta3$ is a good marker for progressive malignant melanomas. It is also known that $\alpha\upsilon\beta6$ is involved in the mechanisms of actual tumour development and in the mechanisms of the invasion of healthy tissue by degenerate cells, metastasis.

A combined therapy aimed both at the angiogenesis of the tumour tissue and at controlling the tumour tissue per se has to date been described only through the combined use of $\alpha\upsilon\beta3$ integrin inhibitors with cytotoxic substances (chemotherapy) or by irradiation (radiotherapy).

It has been found, surprisingly, that the use of selective $\alpha\upsilon\beta3$ integrin inhibitors and the use of selective $\alpha\upsilon\beta6$ integrin inhibitors is suitable for producing a pharmaceutical for such a combined therapy. A synergistic effect is observed. The high selectivity of the inhibition of the $\alpha\upsilon\beta3$ and $\alpha\upsilon\beta6$ integrin receptors means that there is no further inhibition of other integrins—such as, for example, $\alpha5\beta1$ or $\alpha IIb\beta3$, which have important and critical functions for example in normal tissue.

It has also been found that the use of selective $\alpha\upsilon\beta5$ integrin inhibitors and the use of selective $\alpha\upsilon\beta6$ integrin inhibitors is likewise suitable for producing a pharmaceutical for such a combined therapy, as well as the combined use of selective $\alpha\upsilon\beta3$, $\alpha\upsilon\beta5$ and $\alpha\upsilon\beta6$ integrin inhibitors. A synergistic effect is observed in each case.

The compounds of the formula I have at least one chiral centre and can therefore occur in several stereoisomeric forms. All these forms (for example D and L forms) and mixtures thereof (for example the DL forms) are included in the formula.

The compounds of the invention also include so-called prodrug derivatives, that is to say compounds of the formula I which have been modified with, for example, alkyl or acyl groups, sugars or oligopeptides and which are rapidly cleaved in the body to give the active compounds according to the invention. It is also possible for free amino groups or free hydroxy groups or substituents of compounds of the formula I to be provided with appropriate protective groups.

Solvates of the compounds of the formula I mean adducts of inert solvent molecules with the compounds of the formula I, which are formed because of their mutual attractions. Examples of solvates are mono- or dihydrates or addition compounds with alcohols, such as, for example, with methanol or ethanol.

The invention relates to the compounds of formula I and their salts and solvates and to a process for preparing compounds of the formula I and their salts and solvates, characterized in that (a) a compound of the formula II

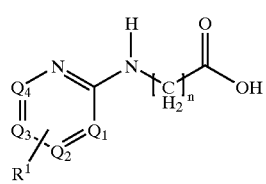

II in which $Q_1$, $Q_2$, $Q_3$, $Q_4$, $R^1$ and n have the meanings stated in claim 1, is reacted with a compound of the formula III

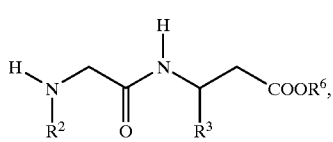

III in which $R^2$, $R^3$, $R^4$, $R^5$ and $R^6$ have the meanings stated in claim 1, and where appropriate, the radical $R^6 \neq H$ is converted in to the radical $R^6 = H$, (b) a compound of the formula IV

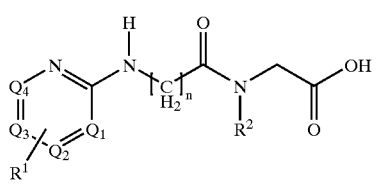

IV in which $Q_1$, $Q_2$, $Q_3$, $Q_4$, $R^1$, and $R^2$ and n have the meanings stated in claim 1, is reacted with a compound of the formula V

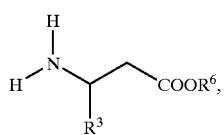

V in which $R^3$, $R^4$, $R^5$ and $R^6$ have the meanings stated in claim 1, and where appropriate, the radical $R^6 \neq H$ is converted into the radical $R^6 = H$, or (c) one or more radicals $R^1$, $R^2$, $R^3$, $R^4$ and/or $R^5$ in a compound of the formula I are converted into one or more radicals $R^1$, $R^2$, $R^3$, $R^4$ and/or $R^5$ by, for example, i) alkylating a hydroxyl group,
  ii) hydrolyzing an ester group to a carboxyl group,
  iii) esterifying a carboxyl group,
  iv) alkylating an amino group or
  v) acylating am amino group, and/or a basic or acidic compound of the formula I is converted by treatment with an acid or base into one of its salts or solvates.

In the above formulae, A is alkyl, is linear or branched, and has 1 to 6, preferably 1, 2, 3, 4, 5 or 6, C atoms. A is preferably methyl, also ethyl, n-propyl, isopropyl, n-butyl, sec-butyl or tert-butyl, in addition pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl. A is particularly preferably methyl, ethyl, isopropyl, n-propyl, n-butyl or tert-butyl.

Ar is aryl which is unsubstituted or mono-, di- or trisubstituted by A, $CF_3$, OH, OA, $OCF_3$, CN or $NO_2$ or Hal, with aryl being phenyl, naphthyl, anthryl or biphenylyl. Ar is preferably phenyl or naphthyl each of which is unsubstituted or mono-, di- or trisubstituted by A, $CF_3$, OH, OA, $OCF_3$, CN or $NO_2$ or Hal.

Ar is therefore preferably phenyl, o-, m- or p-methylphenyl, o-, m- or p-ethylphenyl, o-, m- or p-propyl-phenyl, o-, m- or p-isopropylphenyl, o-, m- or p-tert-butylphenyl, o-, m- or p-hydroxyphenyl, o-, m- or p-methoxyphenyl, o- , m- or p-ethoxyphenyl, o-, m- or p-trifluoromethylphenyl, o-, m- or p-fluorophenyl, o-, m- or p-chlorophenyl, o-, m- or p-bromophenyl, also preferably 2,3-, 2,4-, 2,5-, 2,6-, 3,4- or 3,5-dimethylphenyl, 2,3-, 2,4-, 2,5- , 2,6-, 3,4- or 3,5-dihydroxyphenyl, 2,3-, 2,4-, 2,5-, 2,6-, 3,4- or 3,5-difluorophenyl, 2,3-, 2,4-, 2,5-, 2,6-, 3,4or 3,5-dichlorophenyl, 2,3-, 2,4-, 2,5-, 2,6-, 3,4- or 3,5-dibromophenyl, 2,3-, 2,4-, 2,5-, 2,6-, 3,4- or 3,5-dimethoxyphenyl or 3-chloro-4-fluorophenyl, 4-fluoro-2-hydroxyphenyl, naphthalen-1-yl, naphthalen-2-yl or 2-, 3-, 4-, 5-, 6-, 7- or 8-methylnaphthalen-1-yl, 2-, 3-, 4-, 5-, 6-, 7- or 8-ethylnaphthalen-1-yl, 2-, 3-, 4-, 5-, 6-, 7- or 8-chloronaphthalen-1-yl, 2-, 3-, 4-, 5-, 6-, 7- or 8-fluoronaphthalen-1-yl, 2-, 3-, 4-, 5-, 6-, 7- or 8-bromonaphthalen-1-yl, 2-, 3-, 4-, 5-, 6-, 7- or 8-hydroxynapthalen-1-yl, 1-, 3-, 4-, 5-, 6-, 7-, or 8-methylnaphthalen-2-yl, 1-, 3-, 4-, 5-, 6-, 7-, 8-ethylnaphthalen-2-yl, 1-, 3-, 4-, 5-, 6-, 7- or 8-chloronaphthalen-2yl, 1-, 3-, 4-, 5-, 6-, 7- or 8-fluoronaphthalen-2-yl, 1-, 3-, 4-, 5-, 6-, 7- or 8-bromonaphthalen-2-yl, 1-, 3-, 4-, 5-, 6-, 7- or 8-hydroxynaphthalen-2yl. Ar is very particularly preferably phenyl, o-, m- or p-fluorophenyl, m- or p-chlorophenyl, p-methylphenyl, p-trifluoromethylphenyl, 3--chloro-4-fluorophenyl, 4-fluoro-2-hydroxyphenyl, naphthalen-1-yl or naphthalen-2-yl.

Ar in $—(CH_2)_m—$Ar has one of the preferred meanings stated above, it being possible for m to 1 or 2. Benzyl is particularly preferred for $—(CH_2)_m—$Ar.

It is possible in $—(CH_2)_m—$OH for m to be 1, 2, 3 or 4. $—(CH_2)_m—$OH is preferably hydroxymethyl, hydroxyethyl, hydroxypropyl or hydroxybutyl, very particularly preferably hydroxyethyl.

A in $—(CH_2)_m—O—C(O)A$ has one of the preferred meanings stated above, it being possible for m to be 1 or 2. It is particularly preferred for A to be tert-butyl and m to be 1.

Hal is preferably F, Cl or bromine.

n is 2, 3, 4, 5 or 6, particularly preferably 3, 4 or 5.

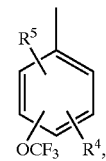

is preferably 3-(trifluoromethoxy)- or 4-(trifluoro-methoxy) phenyl.

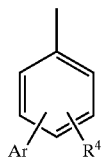

is preferably biphenyl-4-yl, 4'-fluorobiphenyl-4-yl, 4'-fluorobiphenyl-3-yl, 3'-fluorobiphenyl-4-yl, 2'-fluorobiphenyl-4-yl, 4'-chlorobiphenyl-4-yl, 3'-chlorophenyl-4-yl, 4'-methylbiphenyl-4-yl, 4'-(trifluoromethyl)biphenyl-4-yl, 3'-chloro-4'-fluorobiphenyl-4-yl, 4'-fluoro-2-hydroxybiphenyl-4-yl, 4'-fluoro-2'-hydroxybiphenyl-4-yl, 4'-fluoro-2'-hydroxybiphenyl-3-yl, 4-(naphthalen-1-yl)phenyl, 4-(naphthalen-2-yl)phenyl or 4-(naphthalen-1-yl)-3-hydroxyphenyl.

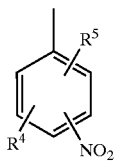

is preferably, 2-, 3- or 4-nitrophenyl, 4-methyl-3-nitrophenyl, 4-chloro-3-nitrophenyl, 3-nitro-2-hydroxyphenyl or 3-bromo-6-hydroxy-5-nitrophenyl.

$Q_1$, $Q_2$, $Q_3$ or $Q_4$ are each, independently of one another, CH or N. $Q_1$ is preferably CH or N, $Q_2$ is preferably CH, $Q_3$ is preferably CH and $Q_4$ is preferably CH. It is very particularly preferred for $Q_1$, $Q_2$, $Q_3$ and $Q_4$ to be CH.

$R^1$ is H, A, Ar, Hal, OH, OA, $CF_3$ or $OCF_3$, where A, Ar or Hal have the preferred or particularly preferred meanings stated above. $R^1$ is preferably H or A. The preferred positions for the substituents $R^1$ are position 4 or 6. Position 4 on the ring system [lacuna] particularly preferred.

$R^2$ is preferably H or A, particularly preferably H.

$R^3$ is

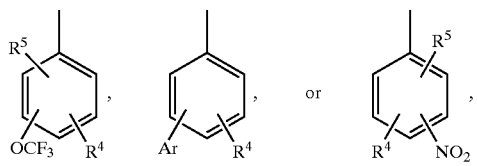

where $R^4$ and $R^5$ are, independently of one another, H, A, Hal, OH, OA, $CF_3$, $OCF_3$, CN, $NH_2$, NHA, $NA_2$ or NH—C(O)A, and AR has one of the meanings stated above.

$R^4$ is particularly preferably H, A, OH or Hal.

$R^5$ is particularly preferably H or OH.

$R^4$ and $R^5$ are particularly preferably H in

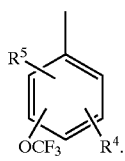

It is particularly preferred for $R^4$ to be H or OH and Ar to be phenyl which is unsubstituted or mono- or disubstituted by Hal, A or $CF_3$, or unsubstituted naphthyl is

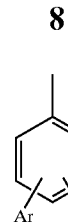

It is particularly preferred for $R^4$ to be H, A or Hal and $R^5$ to be H or OH in

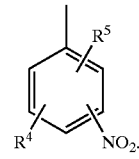

$R^3$ is preferably 2-, 3- or 4-trifluoromethoxyphenyl, 2-, 3- or 4-nitrophenyl, biphenyl-3-yl, biphenyl-4-yl, 3-methyl-, 4-methyl-, 5-methyl- or 6-methyl-2-(trifluoromethoxy)phenyl, 3-ethyl-, 4-ethyl-, 5-ethyl- or 6-ethyl-2-(trifluoromethoxy)phenyl, 2-methyl-, 4-methyl-, 5-methyl- or 6-methyl-3-(trifluoromethoxy)-phenyl, 2-ethyl-, 4-ethyl-, 5-ethyl- or 6-ethyl-3-(trifluoromethoxy)phenyl, 2-methyl-, 3-methyl-, 5-methyl- or 6-methyl-4-(trifluoromethoxy)phenyl, 2-ethyl-, 3-ethyl-, 5-ethyl- or 6-ethyl-4-(trifluoromethoxy)phenyl, 3-methyl-, 4-methyl-, 5-methyl- or 6-methyl-2-nitrophenyl, 3-ethyl-, 4-ethyl-, 5-ethyl- or 6-ethyl-2-nitrophenyl, 2-methyl-, 4-methyl-, 5-methyl- or 6-methyl-3-nitrophenyl, 2-ethyl-, 4-ethyl-, 5-ethyl- or 6-ethyl-3-nitrophenyl, 2-methyl-, 3-methyl-, 5-methyl- or 6-methyl-4-nitrophenyl, 2-ethyl-, 3-ethyl-, 5-ethyl- or 6-ethyl-4-nitrophenyl, 3-chloro-, 4-chloro-, 5-chloro- or 6-chloro-2-nitrophenyl, 2-chloro-, 4-chloro-, 5-chloro- or 6-chloro-3-nitrophenyl, 2-chloro-, 3-chloro-, 5-chloro- or 6-chloro-4-nitrophenyl, 3-nitro-2-hydroxyphenyl, 3-bromo-6-hydroxy-5-nitrophenyl, 4'-fluorobiphenyl-4-yl, 4'-fluorobiphenyl-3-yl, 3'-fluorobiphenyl-4-yl, 2'-fluorobiphenyl-4-yl, 4'-chloro-biphenyl-4-yl, 3'-chlorobiphenyl-4-yl, 4'-methyl-biphenyl-4-yl, 4'-(trifluoromethyl)biphenyl-4-yl, 3'-chloro-4'-fluorobiphenyl-4-yl, 4'-fluoro-2-hydroxybiphenyl-4-yl, 4'-fluoro-2'-hydroxybiphenyl-4-yl, 4'-fluoro-2'-hydroxybiphenyl-3-yl, 4-(naphthalen-1-yl)phenyl, 4-(naphthalen-2-yl)phenyl or 4-(naphthalen-1-yl)-3-hydroxyphenyl.

Particularly preferred meanings for $R^3$ are 4-(trifluoromethoxy)phenyl, 3-(trifluoromethoxy)phenyl, 2-nitrophenyl, 3-nitrophenyl, 4-nitrophenyl, biphenyl-4-yl, 4-methyl-3-nitrophenyl, 4-fluoro-2-hydroxyphenyl or 4-chloro-3-nitrophenyl, 4'-fluorobiphenyl-4-yl, 4'-fluorobiphenyl-3-yl, 3'-fluorobiphenyl-4-yl, 2'-fluorobiphenyl-4-yl, 4'-chlorobiphenyl-4-yl, 3'-chlorobiphenyl-4-yl, 4'-methylbiphenyl-4-yl, 4'-(trifluoromethyl)biphenyl-4-yl, 3'-chloro-4'-fluorobiphenyl-4-yl, 4'-fluoro-2-hydroxybiphenyl-4-yl, 4'-fluoro-2'-hydroxybiphenyl-4-yl, 4'-fluoro-2'-hydroxybiphenyl-3-yl, 4-(naphthalen-1-yl)phenyl, 4-(naphthalen-2-yl)phenyl or 4-(naphthalen-1-yl)-3-hydroxyphenyl or 3-bromo-6-hydroxy-5-nitrophenyl.

$R^6$ is H, A, —$(CH_2)_m$—OH, —$(CH_2)_m$—O—C(O)A or —$(CH_2)_m$—Ar, where A, —$(CH_2)_m$—OH, —$(CH_2)_m$—O—C(O)A or —$(CH_2)_m$—Ar have one of the preferred or particularly preferred meanings stated above.

Compounds of the formula I in which $R^6$ is preferably A, —$(CH_2)_m$—OH, —$(CH_2)_m$—O—C(O)A or —$(CH_2)_m$—Ar, and their solvates, are so-called prodrugs, that is to say they are inactive in in vitro tests because they mask the biologically active carboxyl group. However, prodrugs are converted metabolically in the body into the biologically active form. The corresponding free acid which corresponds to a compound of the formula I with $R^6$=H, and its salts and solvates, is active in vitro.

Accordingly, the invention particularly relates to those compounds of the formula I in which at least one of the said radicals has one of the preferred meanings stated hereinbefore. Some preferred groups of compounds can be expressed by the following part-formulae Ia to Ik which correspond to formula I and in which the undefined radicals have the meaning stated for formula I, but in which in Ia

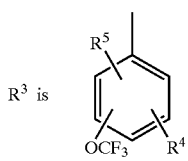

In Ib

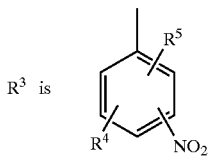

In Ic

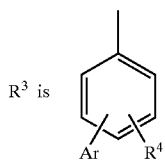

In Id $Q_1$, $Q_2$, $Q_3$ and $Q_4$ of the formula I are CH.

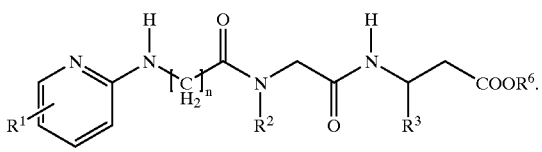

In Ie $Q_1$ is N and $Q_2$, $Q_3$ and $Q_4$ of the formula I are CH.

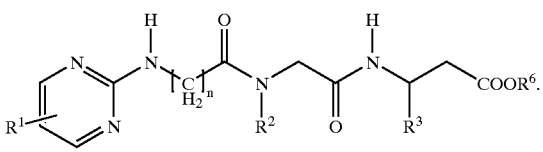

In If $R^1$ is H or A and

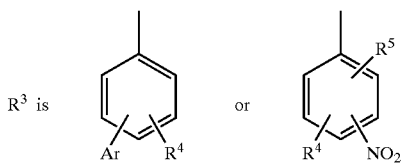

In Ig $R^1$ is H or A,

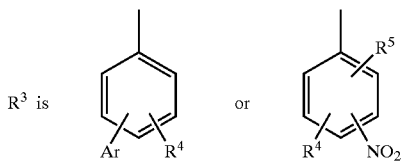

and $Q_1$ is N and $Q_2$, $Q_3$ and $Q_4$ are CH.

In Ih $R^1$ is H or A, $Q_1$, $Q_2$, $Q_3$ and $Q_4$ are CH and

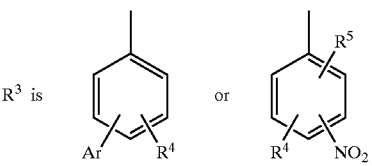

In Ii $R^1$ is H or A and

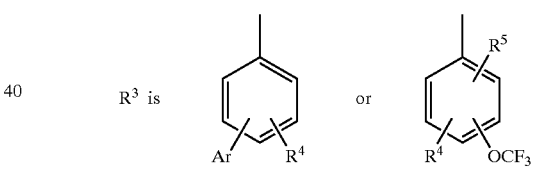

In Ik $R^1$ is H or A and

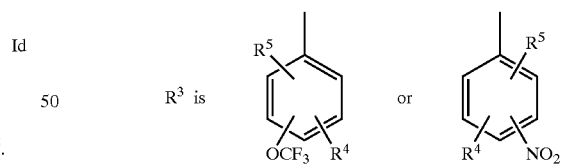

Particularly preferred compounds of the formula Ia are
3-{2-[4-(4-methylpyridin-2-ylamino)butyrylamino]acetylamino}-3-(4-trifluoromethoxyphenyl)propionic acid,
3-{2-[5-(4-methylpyridin-2-ylamino)pentanoylamino]acetylamino}-3-(4-(trifluoromethoxyphenyl)propionic acid,
3-{2-[5-(4-methylpyridin-2-ylamino)pentanoylamino]acetylamino}-3-(3-trifluoromethoxyphenyl)propionic acid or
3-{2-[4-(4-methylpyridin-2-ylamino)butyrylamino]acetylamino}-3-(3-trifluoromethoxyphenyl)propionic acid and their physiologically acceptable salts and solvates.

Particularly preferred compounds of the formula Ib are
3-(4-methyl-3-nitrophenyl)-3-{2-[4-(pyridin-2-ylamino)-butyrylamino]acetylamino}propionic acid,
3-(4-methyl-3-nitrophenyl)-3-{2-[5-(pyridin-2-ylamino)-pentanoylamino]acetylamino}propionic acid,
3-(4-methyl-3-nitrophenyl)-3-{2-[5-(4-methylpyridin-2-ylamino)pentanoylamino]acetylamino}propionic acid,
3-(4-methyl-3-nitrophenyl)-3-{2-[4-(4-methylpyridin-2-ylamino)butyrylamino]acetylamino}propionic acid,
3-(2-nitrophenyl)-3-{2-[5-(pyridin-2-ylamino)pentanoylamino]acetylamino}propionic acid,
3-{2-[4-(4-methylpyridin-2-ylamino)butyrylamino]acetylamino}-3-(2-nitrophenyl)propionic acid,
3-{2-[5-(4-methylpyridin-2-ylamino)pentanoylamino]acetylamino}-3-(2-nitrophenyl)propionic acid,
3-(2-nitrophenyl)-3-{2-[4-(pyridin-2-ylamino)butyrylamino]acetylamino}propionic acid,
3-(3-nitrophenyl)-3-{2-[4-(4-methylpyridin-2-ylamino)butyrylamino]acetylamino}propionic acid,
3-(3-nitrophenyl)-3-{2-[5-(4-methylpyridin-2-ylamino)pentanoylamino]acetylamino}propionic acid,
3-(4-methyl-3-nitrophenyl)-3-{2-[4-(6-methylpyridin-2-ylamino)butyrylamino]acetylamino}propionic acid,
methyl 3-(4-methyl-3-nitrophenyl)-3-{2-[5-(4-methylpyridin-2-ylamino)pentanoylamino]acetylamino}propionate,
3-(4-methyl-3-nitrophenyl)-3-{2-[5-(6-methylpyridin-2-ylamino)pentanoylamino]acetylamino}propionic acid,
3-(4-chloro-3-nitrophenyl)-3-{2-[5-(4-methylpyridin-2-ylamino)pentanoylamino]acetylamino}propionic acid,
3-(4-methyl-3-nitrophenyl)-3-{2-[4-(pyrimidin-2-ylamino)butyrylamino]acetylamino}propionic acid or
3-(4-methyl-3-nitrophenyl)-3-{2-[5-(pyrimidin-2-ylamino)pentanoylamino]acetylamino}propionic acid,
and their physiologically acceptable salts and solvates.

Particularly preferred compounds of the formula Ic are
3-{2-[4-(4-methylpyridin-2-ylamino)butyrylamino]acetylamino}-3-(4-biphenylyl)propionic acid,
3-{2-[4-(pyridin-2-ylamino)butyrylamino]acetylamino}-3-(4-biphenylyl)propionic acid,
3-{2-[5-(pyrimidin-2-ylamino)pentanoylamino]acetylamino}-3-(4-biphenylyl)propionic acid,
3-{2-[4-(pyrimidin-2-ylamino)butyrylamino]acetylamino}-3-(4-biphenylyl)propionic acid,
3-{2-[5-(pyridin-2-ylamino)pentanoylamino]acetylamino}-3-(4-biphenylyl)propionic acid or
3-{2-[4-(4-methylpyridin-2-ylamino)butyrylamino]acetylamino}-3-(4-biphenylyl)propionic acid and their physiologically acceptable salts and solvates.

Particularly preferred compounds of the formula Id are
3-{2-[4-(4-methylpyridin-2-ylamino)butyrylamino]acetylamino}-3-(4-trifluoromethoxyphenyl)propionic acid,
3-{2-[5-(4-methylpyridin-2-ylamino)pentanoylamino]acetylamino}-3-(4-trifluoromethoxyphenyl)propionic acid,
3-{2-[5-(4-methylpyridin-2-ylamino)pentanoylamino]acetylamino}-3-(3-trifluoromethoxyphenyl)propionic acid,
3-{2-[4-(4-methylpyridin-2-ylamino)butyrylamino]acetylamino}-3-(3-trifluoromethoxyphenyl)propionic acid,
3-(4-methyl-3-nitrophenyl)-3-{2-[4-(pyridin-2-ylamino)butyrylamino]acetylamino}propionic acid,
3-(4-methyl-3-nitrophenyl)-3-{2-[5-(pyridin-2-ylamino)pentanoylamino]acetylamino}propionic acid,
3-(4-methyl-3-nitrophenyl)-3-{2-[5-(4-methylpyridin-2-ylamino)pentanoylamino]acetylamino}propionic acid,
3-(4-methyl-3-nitrophenyl)-3-{2-[4-(4-methylpyridin-2-ylamino)butyrylamino]acetylamino}propionic acid,
3-(2-nitrophenyl)-3-{2-[5-pyridin-2-ylamino)pentanoylamino]acetylamino}propionic acid,
3-{2-[4-(4-methylpyridin-2-ylamino)butyrylamino]acetylamino}-3-(2-nitrophenyl)propionic acid,
3-{2-[5-(4-methylpyridin-2-ylamino)pentanoylamino]acetylamino}-3-(2-nitrophenyl)propionic acid,
3-(2-nitrophenyl)-3-{2-[4-(pyridin-2-ylamino)butyrylamino]acetylamino}propionic acid,
3-(3-nitrophenyl)-3-{2-[4-(4-methylpyridin-2-ylamino)butyrylamino]acetylamino}propionic acid,
3-(3-nitrophenyl)-3-{2-[5-(4-methylpyridin-2-ylamino)pentanoylamino]acetylamino}propionic acid,
3-(4-methyl-3-nitrophenyl)-3-{2-[4-(6-methylpyridin-2-ylamino)butyrylamino]acetylamino}propionic acid,
methyl 3-(4-methyl-3-nitrophenyl)-3-{2-[5-(4-methylpyridin-2-ylamino)pentanoylamino]acetylamino}propionic acid,
3-(4-methyl-3-nitrophenyl)-3-{2-[5-(6-methylpyridin-2-ylamino)pentanoylamino]acetylamino}propionic acid,
3-(4-chloro-3-nitrophenyl)-3-{2-[5-(4-methylpyridin-2-ylamino)pentanoylamino]acetylamino}propionic acid,
3-{2-[4-(4-methylpyridin-2-ylamino)butyrylamino]acetylamino}-3-(4-biphenylyl)propionic acid,
3-{2-[4-(pyridin-2-ylamino)butyrylamino]acetylamino}-3-(4-biphenylyl)propionic acid,
3-{2-[5-(pyridin-2-ylamino)pentanoylamino]acetylamino}-3-(4-biphenylyl)propionic acid,
3-{2-[5-(4-methylpyridin-2-ylamino)pentanoylamino]acetylamino}-3-(4-biphenylyl)propionic acid,
and their physiologically acceptable salts and solvates.

Preferred compounds of the formula Ie are
3-(4-methyl-3-nitrophenyl)-3-{2-[4-(pyrimidin-2-ylamino)butyrylamino]acetylamino}propionic acid,
3-(4-methyl-3-nitrophenyl)-3-{2-[5-(pyrimidin-2-ylamino)pentanoylamino]acetylamino}propionic acid,
3-{2-[5-(pyrimidin-2-ylamino)pentanoylamino]acetylamino}-3-(4-biphenylyl)propionic acid or
3-{2-[4-(pyrimidin-2-ylamino)butyrylamino]acetylamino}-3-(4-biphenylyl)propionic acid,
and their physiologically acceptable salts and solvates.

Preferred compounds of the formula If are
3-{2-[4-(pyridin-2-ylamino)butyrylamino]acetylamino}-3-(4-biphenylyl)propionic acid,
3-{2-[5-(4-methylpyridin-2-ylamino)pentanoylamino]acetylamino}-3-(4-biphenylyl)propionic acid,
3-{2-[5-pyridin-2-ylamino)pentanoylamino]acetylamino}-3-(4-biphenylyl)propionic acid or
3-{2-[4-(4-methylpyridin-2-ylamino)butyrylamino]acetylamino}-3-(4-biphenylyl)propionic acid,
and their physiologically acceptable salts and solvates.

The compounds of the formula I according to claim 1 and the starting materials for preparing them are moreover prepared by methods which are known per se and are described in the literature (for example in the standard works such as Houben-Weyl, Methoden der organischen Chemie [Methods of Organic Chemistry], Georg-Thieme-Verlag, Stuttgart), specifically under reaction conditions known and suitable for the said reactions. It is moreover possible to make use of variants which are known per se but are not detailed here.

The starting materials can, if required, also be formed in situ, so that they are not isolated from the reaction mixture but immediately reacted further to give the compounds of the formula I according to claim 1.

It is also possible for a plurality of—identical or different—protective amino and/or hydroxyl groups to be present in the molecular of the starting material. If the protective groups which are present differ from one another, they can in many cases be cleaved off selectively (compare in this connection: T. W. Greene, P. G. M. Wuts, *Protective groups in Organic Chemistry*, 2$^{nd}$ edition, Wiley, New York 1991 or P. J. Kocienski, *Protecting Groups*, 1$^{st}$ edition, Georg Thieme Verlag, Stuttgart—New York, 1994, H. Kunz, H. Waldmann in *Comprehensive Organic Synthesis,* Vol. 6 (ed. B. M. Trost, I. Fleming, E. Winterfeldt), Pergamon, Oxford, 1991, pp. 631–701).

The term "amino protective group" is generally known and refers to groups which are suitable for protecting (blocking) an amino group from chemical reactions. Typical groups of this type are, in particularly, unsubstituted or substituted acyl, aryl, aralkoxymethyl or aralkyl groups. Since the amino protective groups are removed after the required reaction (or sequence of reactions), their nature and size is otherwise not critical; however, those with 1–20, in particular 1–8, C atoms are preferred. The term "acyl group" is to be interpreted in the widest sense in connection with the present process. It includes acyl groups derived from aliphatic, araliphatic, alicyclic, aromatic or heterocyclic carboxylic acids or sulfonic acids, and, in particular, alkoxycarbonyl, alkenyloxycarbonyl, aryloxycarbonyl and, especially, aralkoxycarbonyl groups. Examples of such acyl groups are alkanoyl such as acetyl, propionyl, butyryl; aralkanoyl such as phenylacetyl; aroyl such as benzoyl or toluyl; aryloxyalkanoyl such as phenoxyacetyl; alkoxycarbonyl such as methoxycarbonyl, ethoxycarbonyl, 2,2,2-trichloroethoxycarbonyl, BOC, 2-iodoethoxycarbonyl; alkenyloxycarbonyl such as allyloxycarbonyl (Aloc), aralkyloxycarbonyl such as CBZ (synonymous with Z), 4-methoxybenzyloxycarbonyl (MOZ), 4-nitrobenzyloxycarbonyl or 9-fluorenylmethoxycarbonyl (Fmoc); 2-(phenylsulfonyl)ethoxycarbonyl; trimethylsilylethoxycarbonyl (Teoc) or arylsulfonyl such as 4-methoxy-2,3,6-trimethylphenylsulfonyl (Mtr). Preferred amino protective groups are BOC, Fmoc and Aloc, also CBZ, benzyl and acetyl.

The term "hydroxyl protective group" is likewise generally known and refers to groups which are suitable for protecting a hydroxyl group from chemical reactions. Typical groups of this type are the abovementioned unsubstituted or substituted aryl, aralkyl, aroyl or acyl groups, also alkyl groups, alkyl-, aryl- or aralkylsilyl groups or O,O- or O,S-acetals. The nature and size of the hydroxyl protective groups is not critical because they are removed again after the required chemical reaction or sequence of reactions; preferred groups have 1–20, in particular 1–10, C atoms. Examples of hydroxyl protective groups include aralkyl groups such as benzyl, 4-methoxybenzyl or 2,4-dimethoxybenzyl, aroyl groups such as benzoyl or p-nitrobenzoyl, acyl groups such as acetyl or pivaloyl, p-toluenesulfonyl, alkyl groups such as methyl or tert-butyl, but also allyl, alkylsilyl groups such as trimethylsilyl (TMS), triisopropylsilyl (TIPS), tert-butyldimethylsilyl (TBS) or triethylsilyl, trimethylsilylethyl, aralkylsilyl groups such as tert-butyldiphenylsilyl (TBDPS), cyclic acetals such as isopropylidene, cyclopentylidene, cyclohexylidene, benzylidene, p-methoxybenzylidene or o,p-dimethoxybenzylidene acetal, acyclic acetals such as tetrahydropyranyl (Thp), methoxymethyl (MOM), methoxyethoxymethyl (MEM), benzyloxymethyl (BOM) or methylthiomethyl (MTM). Particularly preferred hydroxyl protective groups are benzyl, acetyl, tert-butyl or TBS.

The liberation of the compounds of the formula I from their functional derivatives is known from the literature for the particular protective group used (for example T. W. Greene, P. G. M. Wuts, *Protective Groups in Organic Chemistry*, 2$^{nd}$ edition, Wiley, New York 1991 or P. J. Kocienski, *Protecting Groups,* 1$^{st}$ edition, Georg Thieme Verlag, Stuttgart—New York, 1994). It is moreover possible to make use of variants which are known per se but are not detailed here.

The BOC and O-tert-butyl groups can be cleaved off, for example, preferably with TFA in dichloromethane or with approximately 3 to 5N HCl in dioxane in 15–30° C., and the Fmoc group with an approximately 5 to 50% strength solution of dimethylamine, diethylamine or piperidine in DMF at 15–30° C. The Aloc group can be cleaved under mild conditions with noble metal catalysis in chloroform at 20–30° C. A preferred catalyst is tetrakis (triphenylphosphine)palladium(0).

The starting compounds of the formula II to V are usually known. If they are novel, they can, however, be prepared by methods known per se.

Compounds of the formula II are obtained, for example, from coupling the corresponding 2-amino compound of the heterocycle in which $Q_1$, $Q_2$, $Q_3$ or $Q_4$ have the meanings stated in formula I with the appropriate n-bromo carboxylates (Br—$[CH_2]_n$—COOPG$^1$, where PG$^1$ is a hydroxyl protective group as described above) n the presence of a base, and subsequently cleaving off the protective group under standard conditions.

Compounds of the formula IV are obtained by a peptide-analogous coupling of compounds of the formula II with a glycine derivative $H_2N$—$CH_2$—COOPG$^2$, where PG$^2$ is a hydroxyl protective group as described above, under standard conditions.

Compounds of the formula V (β-amino acids) can be prepared in analogy to Skinner et al., J. Org. Chem. 1960, 25, 1756. The reaction of the corresponding aldehyde $R^3$—CHO with malonic acid and ammonium acetate in a suitable solvent, particularly preferably alcohols such as, for example, ethanol, produces the β-amino acid of the formula V where $R^6$ is H. Esterification of this free acid of the formula V under standard conditions affords compounds of the formula V where $R^6$ is A or —$(CH_2)_m$—Ar.

Compounds of the formula III are prepared by coupling the β-amino acids of the formula V which are protected on the acid functionality, either by an appropriate protective group or, if $R^6$ is A, —$(CH_2)_m$—OH, —$(CH_2)_m$—O—C(O)A or —$(CH_2)_m$—Ar, with a glycine derivative PG$^3$—NH—$CH_2$—COOH. The substituent PG$^3$ in the glycine derivative PG$^3$—NH—$CH_2$—COOH is an amino protective group as described above, which is then cleaved off. Conventional methods of peptide synthesis are described, for example, in Houben-Weyl, l.c. [sic], volume 15/II, 1974, pages 1 to 806.

Compounds of the formula I can be obtained by reacting a compound of the formula II with a compound of the formula III, and then cleaving off a protective group, or converting the radical $R^6$ which is A, —$(CH_2)_m$—OH, —$(CH_2)_m$—O—C(O)A or —$(CH_2)_m$—Ar into the radical $R^6$=H.

The compounds of the formula I can likewise be obtained by reacting a compound of the formula IV with a compound of the formula V, and then cleaving off a protective group, or converting the radical $R^6$ which is A, —$(CH_2)_m$—OH, —$(CH_2)_m$—O—C(O)A or —$(CH_2)_m$—Ar into the radical $R^6$=H.

The coupling reaction preferably takes place in the presence of a dehydrating agent, for example of a carbodiimide such as dicyclohexylcarbodiimie (DCC), N-(3- dimethylaminopropyl)-N'-ethylcarbodiimide hydrocyhloride (EDC) or diisopropylcarbodiimide (DIC), also, for example, propanephosphonic anhydride (compare Angew. Chem. 1980, 92, 129), diphenylphosphoryl azide or 2-ethoxy-N-ethoxycarbonyl-1,2-dihydroquinoline, in an inert solvent, for example a halogenated hydrocarbon such as dichloromethane, an ether such as tetrahydrofuran or dioxane, an amide such as DMF or dimethylacetamide, a nitrile such as acetonitrile, in dimethyl sulfoxide or in the presence of these solvents, at temperatures between about −10 and 40, preferably between 0 and 30°. The reaction time depends on the conditions used and is between a few minutes and several days. It has proved particularly advantageous to add the coupling reagent TBTU (O-(benzotriazol-1-yl)-N,N,N',N'-tetramethyluronium tetrafluoroborate) or O-(benzotriazol-1-yl)-N,N,N',N'-tetramethyluronium hexafluorophosphate, because only a small amount of racemization occurs in the presence of one of these compounds, and no cytotoxic byproducts are formed.

In place of compounds of the formulae II and/or IV, it is also possible to employ derivatives of compounds of the formula II and/or IV, preferably a preactivated carboxylic acid, or a carbonyl halide, a symmetrical or mixed anhydride or an active ester. Residues of this type for activating the carboxyl group in typical acylation reactions are described in the literature (for example in the standard works such as Houben-Weyl, Methoden der organischen Chemie, Georg-Thieme-Verlag, Stuttgart). Activated esters are preferably formed in situ, for example by adding HOBt (1-hydroxybenzotriazole) or N-hydroxysuccinimide.

The reaction normally takes place in an inert solvent and, when a carbonyl halide is used, in the presence of an acid-binding agent, preferably an organic base such as triethylamine, dimethylaniline, pyridine or quinoline.

It may also be beneficial to add an alkali metal or alkaline earth metal hydroxide, carbonate or bicarbonate or another weak acid salt of the alkali metals or alkaline earth metals, preferably of potassium, sodium, calcium or caesium.

A base of the formula I can be converted with an acid into the relevant acid addition salt, for example by reacting equivalent amounts of the base and of the acid in an inert solvent such as ethanol, and then evaporating. Acids particularly suitable for this reaction are those which provide physiologically acceptable salts. Thus, it is possible to use inorganic acids, for example sulfuric acid, sulfurous acid, dithionic acid, nitric acid, hydrohalic acids such as hydrochloric acid, or hydrobromic acid, phosphoric acids such as, for example, ortho-phosphoric acid, sulfamic acid, also organic acids, in particular aliphatic, alicyclic, araliphatic, aromatic or heterocyclic mono- or polybasic carboxylic, sulfonic or sulfuric acids, for example formic acid, acetic acid, propionic acid, hexanoic acid, octanoic acid, decanoic acid, hexadecanoic acid, octadecanoic acid, pivalic acid, diethylacetic acid, malonic acid, succinic acid, pimelic acid, furamic acid, maleic acid, lactic acid, tartaric acid, malic acid, citric acid, gluconic acid, ascorbic acid, nicotinic acid, isonicotinic acid, methane- or ethanesulfonic acid, benzenesulfonic acid, trimethoxybenzoic acid, adamantanecarboxylic acid, p-toluenesulfonic acid, glycolic acid, embonic acid, chlorophenoxyacetic acid, aspartic acid, glutamic acid, proline, glyoxylic acid, palmitic acid, parachlorophenoxy-isobutyric acid, cyclohexanecarboxylic acid, glucose 1-phosphate, naphthalenemono- and -disulfonic acids or lauryl sulfuric acid. Salts with physiologically unacceptable acids, for example picrates, can be used to isolate and/or purify the compounds of the formula I. On the other hand, compounds of the formula I can be converted with bases (for example sodium or potassium hydroxide or carbonate) into the corresponding metal, in particular alkali metal or alkaline earth metal, or into the corresponding ammonium salts.

The invention also relates to the compounds of the formula I and their physiologically acceptable salts or solvates as active pharmaceutical ingredients.

The invention further relates to compounds of the formula I and their physiologically acceptable salts or solvates as integrin inhibitors.

The invention also relates to the compounds of the formula I and their physiologically acceptable salts or solvates for use for controlling diseases.

The invention further relates to the use of a combination of selective integrin inhibitors selected from the group of selective $\alpha v \beta 3$ integrin inhibitors combined with selective $\alpha v \beta 6$ integrin inhibitors, selective $\alpha v \beta 5$ integrin inhibitors combined with selective $\alpha v \beta 6$ integrin inhibitors or selective $\alpha v \beta 3$ integrin inhibitors combined with selective $\alpha v \beta 5$ integrin inhibitors combined with selective $\alpha v \beta 6$ integrin inhibitors, for producing a pharmaceutical for controlling pathological processes influenced by the integrins $\alpha v \beta 3$ and/or $\alpha v \beta 5$ and $\alpha v \beta 6$.

The invention relates to the use of a combination of selective integrin inhibitors selected from the group of selective $\alpha v \beta 3$ integrin inhibitors combined with selective $\alpha v \beta 6$ integrin inhibitors, selective $\alpha v \beta 5$ integrin inhibitors combined with selective $\alpha v \beta 6$ integrin inhibitors or selective $\alpha v \beta 3$ integrin inhibitors combined with selective $\alpha v \beta 5$ integrin inhibitors and combined with selective $\alpha v \beta 6$ integrin inhibitors, for producing a pharmaceutical for cancer therapy, there being suppression on the one hand of angiogenesis of the blood vessels growing into the tumour through inhibition of the $\alpha v \beta 3$ integrin receptor and/or of the $\alpha v \beta 5$ integrin receptor, and on the other hand of tumor development through inhibition of the $\alpha v \beta 6$ integrin receptor.

The invention relates to the use of a combination of selective $\alpha v \beta 3$ integrin inhibitors and/or selective $\alpha v \beta 5$ and selective $\alpha v \beta 6$ integrin inhibitors for producing a pharmaceutical for controlling diseases associated with cancer, such as metastases of solid tumours, angiofibromatosis, retrolental fibroplasia, hemangioma or Kaposi's sarcoma.

Selected compounds of the formula I which are, in particular, selective $\alpha v \beta 3$ and $\alpha v \beta 6$ integrin receptor inhibitors are listed below:
a) 3-{2-[5-(4-methylpyridin-2-ylamino)pentanoylamino]acetylamino}-3-(4-chloro-3-nitrophenyl)propionic acid trifluoroacetate;
b) 3-(4-methyl-3-nitrophenyl)-3-{2-[5-(4-methylpyridin-2-ylamino)pentanoylamino]acetylamino}propionic acid trifluoroacetate;
c) 3-(4-methyl-3-nitrophenyl)-3-{2-[4-pyridin-2-ylamino)butyrylamino]acetylamino}propionic acid trifluoroacetate
d) 3-{2-[5-(4-methylpyridin-2-ylamino)pentanoylamino]acetylamino}-3-(4-trifluoromethoxyphenyl)propionic acid trifluoroacetate or
e) 3-(biphenyl-4-yl)-3-{2-[5-(pyridin-2-ylamino)pentanoylamino]acetylamino}propionic acid trifluoroacetate.

Selected compounds of the formula I which are, in particular, selective $\alpha v \beta 5$ and $\alpha v \beta 6$ integrin receptor inhibitors are listed below:
a) 3-{2-[4-(4-methylpyridin-2-ylamino)butyrylamino]acetylamino}-3-(3-trifluoromethoxyphenyl)propionic acid trifluoroacetate or
b) 3-(3-nitrophenyl)-3-{2-[5-(4-methylpyridin-2-ylamino)pentanoylamino]acetylamino}propionic acid trifluoroacetate.

Selected compounds of the formula I which are, in particular, selective αvβ3, αvβ5 and αvβ6 integrin receptor inhibitors are listed below:
a) 3-{2-[4-(4-methylpyridin-2-ylamino)butyrylamino]acetylamino}-3-(4-methyl-3-nitrophenyl)propionic acid trifluoroacetate;
b) 3-(3-nitrophenyl)-3-{2-[4-(4-methylpyridin-2-ylamino)butyrylamino]acetylamino}propionic acid trifluoroacetate;
c) 3-{2-[4-(4-methylpyridin-2-ylamino)butyrylamino]acetylamino}-3-(4-trifluoromethoxyphenyl)propionic acid trifluoroacetate;
d) 3-{2-[5-(4-methylpyridin-2-ylamino)pentanoylamino]acetylamino}-3-(3-trifluoromethoxyphenyl)propionic acid trifluoroacetate or
e) 3-(3-nitrophenyl)-3-{2-[5-(4-methylpyridin-2-ylamino)pentanoylamino]acetylamino}propionic acid hydrochloride.

Particularly suitable for use for producing a pharmaceutical for a therapy or for controlling pathological processes which can be influenced by the integrins αvβ3 and/or αvβ5 and αvβ6, in particular for a cancer therapy, as described above, are the integrin inhibitors
a) 3-{2-[5-(4-methylpyridin-2-ylamino)pentanoylamino]acetylamino}-3-(4-chloro-3-nitrophenyl)propionic acid trifluoroacetate;
b) 3-(4-methyl-3-nitrophenyl)-3-{2-[5-(4-methylpyridin-2-ylamino)pentanoylamino]acetylamino}propionic acid trifluoroacetate;
c) 3-(4-methyl-3-nitrophenyl)-3-{2-[4-(pyridin-2-ylamino)butyrylamino]acetylamino}propionic acid trifluoroacetate;
d) 3-{2-[5-(4-methylpyridin-2-ylamino)pentanoylamino]acetylamino}-3-(4-trifluoromethoxyphenyl)propionic acid trifluoroacetate;
e) 3-(biphenyl-4-yl)-3-{2-[5-(pyridin-2-ylamino)pentanoylamino]acetylamino}propionic acid trifluoroacetate;
f) 3-{2-[4-(4-methylpyridin-2-ylamino)butyrylamino]acetylamino}-3-(3-trifluoromethoxyphenyl)propionic acid trifluoroacetate;
g) 3-(3-nitrophenyl)-3-{2-[5-(4-methylpyridin-2-ylamino)pentanoylamino]acetylamino}propionic acid trifluoroacetate;
h) 3-{2-[4-(4-methylpyridin-2-ylamino)butyrylamino]acetylamino}-3-(4-methyl-3-nitrophenyl)propionic acid trifluoroacetate;
i) 3-(3-nitrophenyl)-3-{2-[4-(4-methylpyridin-2-ylamino)butyrylamino]acetylamino}propionic acid trifluoroacetate;
j) 3-{2-[4-(4-methylpyridin-2-ylamino)butyrylamino]acetylamino}-3-(4-trifluoromethoxyphenyl)propionic acid trifluoroacetate;
k) 3-{2-[5-(4-methylpyridin-2-ylamino)pentanoylamino]acetylamino}-3-(3-trifluoromethoxyphenyl)propionic acid trifluoroacetate or
l) 3-(3-nitrophenyl)-3-{2-[5-(4-methylpyridin-2-ylamino)pentanoylamino]acetylamino}propionic acid hydrochloride.

The invention further relates to the use of selective integrin inhibitors selected from the group of
a) 3-{2-[5-(4-methylpyridin-2-ylamino)pentanoylamino]acetylamino}-3-(4-chloro-3-nitrophenyl)propionic acid trifluoroacetate;
b) 3-(4-methyl-3-nitrophenyl)-3-{2-[5-(4-methylpyridin-2-ylamino)pentanoylamino]acetylamino}propionic acid trifluoroacetate;
c) 3-(4-methyl-3-nitrophenyl)-3-{2-[4-(pyridin-2-ylamino)butyrylamino]acetylamino}propionic acid trifluoroacetate;
d) 3-{2-[5-(4-methylpyridin-2-ylamino)pentanoylamino]acetylamino}-3-(4-trifluoromethoxyphenyl)propionic acid trifluoroacetate;
e) 3-(biphenyl-4-yl)-3-{2-[5-(pyridin-2-ylamino)pentanoylamino]acetylamino}propionic acid trifluoroacetate;
f) 3-{2-[4-(4-methylpyridin-2-ylamino)butyrylamino]acetylamino}-3-(3-trifluoromethoxyphenyl)propionic acid trifluoroacetate;
g) 3-(3-nitrophenyl)-3-{2-[5-(4-methylpyridin-2-ylamino)pentanoylamino]acetylamino}propionic acid trifluoroacetate;
h) 3-{2-[4-(4-methylpyridin-2-ylamino)butyrylamino]acetylamino}-3-(4-methyl-3-nitrophenyl)propionic acid trifluoroacetate;
i) 3-(3-nitrophenyl)-3-{2-[4-(4-methylpyridin-2-ylamino)butyrylamino]acetylamino}propionic acid trifluoroacetate;
j) 3-{2-[4-(4-methylpyridin-2-ylamino)butyrylamino]acetylamino}-3-(4-trifluoromethoxyphenyl)propionic acid trifluoroacetate;
k) 3-{2-[5-(4-methylpyridin-2-ylamino)pentanoylamino]acetylamino}-3-(3-trifluoromethoxyphenyl)propionic acid trifluoroacetate or
l) 3-(3-nitrophenyl)-3-{2-[5-(4-methylpyridin-2-ylamino)pentanoylamino]acetylamino}propionic acid hydrochloride,
for producing a pharmaceutical for controlling pathological processes influenced by the integrins αvβ3 and/or αvβ5 and αvβ6.

The invention relates to the use of selective integrin inhibitors selected from the group of
a) 3-{2-[5-(4-methylpyridin-2-ylamino)pentanoylamino]acetylamino}-3-(4-chloro-3-nitrophenyl)propionic acid trifluoroacetate;
b) 3-(4-methyl-3-nitrophenyl)-3-{2-[5-(4-methylpyridin-2-ylamino)pentanoylamino]acetylamino}propionic acid trifluoroacetate;
c) 3-(4-methyl-3-nitrophenyl)-3-{2-[4-(pyridin-2-ylamino)butyrylamino]acetylamino}propionic acid trifluoroacetate;
d) 3-{2-[5-(4-methylpyridin-2-ylamino)pentanoylamino]acetylamino}-3-(4-trifluoromethoxyphenyl)propionic acid trifluoroacetate;
e) 3-(biphenyl-4-yl)-3-{2-[5-(pyridin-2-ylamino)pentanoylamino]acetylamino}propionic acid trifluoroacetate;
f) 3-{2-[4-(4-methylpyridin-2-ylamino)butyrylamino]acetylamino}-3-(3-trifluoromethoxyphenyl)propionic acid trifluoroacetate;
g) 3-(3-nitrophenyl)-3-{2-[5-(4-methylpyridin-2-ylamino)pentanoylamino]acetylamino}propionic acid trifluoroacetate;
h) 3-{2-[4-(4-methylpyridin-2-ylamino)butyrylamino]acetylamino}-3-(4-methyl-3-nitrophenyl)propionic acid trifluoroacetate;
i) 3-(3-nitrophenyl)-3-{2-[4-(4-methylpyridin-2-ylamino)butyrylamino]acetylamino}propionic acid trifluoroacetate;
j) 3-{2-[4-(4-methylpyridin-2-ylamino)butyrylamino]acetylamino}-3-(4-trifluoromethoxyphenyl)propionic acid trifluoroacetate;
k) 3-{2-[5-(4-methylpyridin-2-ylamino)pentanoylamino]acetylamino}-3-(3-trifluoromethoxyphenyl)propionic acid trifluoroacetate or l) 3-(3-nitrophenyl)-3-{2-[5-(4-methylpyridin-2-ylamino)pentanoylamino]acetylamino}propionic acid hydrochloride, for producing a pharmaceutical for cancer therapy, there being suppression on the one hand of angiogenesis of the blood vessels growing into the tumour through inhibition of the αvβ3 integrin receptor and/or of the αvβ5 integrin receptor, and on the other hand of tumour development through inhibition of the αvβ6 integrin receptor.

The invention relates to the use of selective αvβ3 integrin inhibitors and/or selective αvβ5 and selective αvβ6 integrin inhibitors selected from the group of a) 3-{2-[5-(4-methylpyridin-2-ylamino)pentanoylamino]acetylamino}-3-(4-chloro-3-nitrophenyl)propionic acid trifluoroacetate;
b) 3-(4-methyl-3-nitrophenyl)-3-{2-[5-(4-methylpyridin-2-ylamino)pentanoylamino]acetylamino}propionic acid trifluoroacetate;
c) 3-(4-methyl-3-nitrophenyl)-3-{2-[4-(pyridin-2-ylamino)butyrylamino]acetylamino}propionic acid trifluoroacetate;
d) 3-{2-[5-(4-methylpyridin-2-ylamino)pentanoylamino]acetylamino}-3-(4-trifluoromethoxyphenyl)propionic acid trifluoroacetate;
e) 3-(biphenyl-4-yl)-3-{2-[5-(pyridin-2-ylamino)pentanoylamino]acetylamino}propionic acid trifluoroacetate;
f) 3-{2-[4-(4-methylpyridin-2-ylamino)butyrylamino]acetylamino}-3-(3-trifluoromethoxyphenyl)propionic acid trifluoroacetate;
g) 3-(3-nitrophenyl)-3-{2-[5-(4-methylpyridin-2-ylamino)pentanoylamino]acetylamino}propionic acid trifluoroacetate;
h) 3-{2-[4-(4-methylpyridin-2-ylamino)butyrylamino]acetylamino}-3-(4-methyl-3-nitrophenyl)propionic acid trifluoroacetate;
i) 3-(3-nitrophenyl)-3-{2-[4-(4-methylpyridin-2-ylamino)butyrylamino]acetylamino}propionic acid trifluoroacetate;
j) 3-{2-[4-(4-methylpyridin-2-ylamino)butyrylamino]acetylamino}-3-(4-trifluoromethoxyphenyl)propionic acid trifluoroacetate;
k) 3-{2-[5-(4-methylpyridin-2-ylamino)pentanoylamino]acetylamino}-3-(3-trifluoromethoxyphenyl)propionic acid trifluoroacetate or
l) 3-(3-nitrophenyl)-3-{2-[5-(4-methylpyridin-2-ylamino)pentanoylamino]acetylamino}propionic acid hydrochloride, for producing a pharmaceutical for controlling diseases which are associated with cancer, such as metastases of solid tumours, angiofibromatosis, retrolental fibroplasia, hemangioma or Kaposi's sarcoma.

Particularly suitable for use for producing a pharmaceutical for cancer therapy, there being suppression on the one hand of angiogenesis of the blood vessels growing into the tumour through inhibition of the αvβ3 integrin receptor, and on the other hand of tumour development through inhibition of the αvβ6 integrin receptor, are the β-alanine derivatives a) 3-{2-[5-(4-methylpyridin-2-ylamino)pentanoylamino]acetylamino}-3-(4-chloro-3-nitrophenyl)propionic acid trifluoroacetate;
b) 3-(4-methyl-3-nitrophenyl)-3-{2-[5-(4-methylpyridin-2-ylamino)pentanoylamino]acetylamino}propionic acid trifluoroacetate;
c) 3-(4-methyl-3-nitrophenyl)-3-{2-[4-(pyridin-2-ylamino)butyrylamino]acetylamino}propionic acid trifluoroacetate;
d) 3-{2-[5-(4-methylpyridin-2-ylamino)pentanoylamino]acetylamino}-3-(4-trifluoromethoxyphenyl)propionic acid trifluoroacetate or
e) 3-(biphenyl-4-yl)-3-{2-[5-(pyridin-2-ylamino)pentanoylamino]acetylamino}propionic acid trifluoroacetate.

Particularly suitable for use for producing a pharmaceutical for cancer therapy, there being suppression on the one hand of angiogenesis of the blood vessels growing into the tumour through inhibition of the αvβ5 integrin receptor, and on the other hand of tumour development through inhibition of the αvβ6 integrin receptor, are the β-alanine derivatives a) 3-{2-[4-(4-methylpyridin-2-ylamino)butyrylamino]acetylamino}-3-(3-trifluoromethoxyphenyl)propionic acid trifluoroacetate or
b) 3-(3-nitrophenyl)-3-{2-[5-(4-methylpyridin-2-ylamino)pentanoylamino]acetylamino}propionic acid trifluoroacetate.

Particularly suitable for use for producing a pharmaceutical for cancer therapy, there being suppression on the one hand of angiogenesis of the blood vessels growing into the tumour through inhibition of the αvβ3 and αvβ5 integrin receptor, and on the other hand of tumour development through inhibition of the αvβ6 integrin receptor, are the β-alanine derivatives a) 3-{2-[4-(4-methylpyridin-2-ylamino)butyrylamino]acetylamino}-3-(4-methyl-3-nitrophenyl)propionic acid trifluoroacetate;
b) 3-(3-nitrophenyl)-3-{2-[4-(4-methylpyridin-2-ylamino)butyrylamino]acetylamino}propionic acid trifluoroacetate;
c) 3-{2-[4-(4-methylpyridin-2-ylamino)butyrylamino]acetylamino}-3-(4-trifluoromethoxyphenyl)propionic acid trifluoroacetate;
d) 3-{2-[5-(4-methylpyridin-2-ylamino)pentanoylamino]acetylamino}-3-(3-trifluoromethoxyphenyl)propionic acid trifluoroacetate or
e) 3-(3-nitrophenyl)-3-{2-[5-(4-methylpyridin-2-ylamino)pentanoylamino]acetylamino}propionic acid hydrochloride.

Also conceivable in addition to the use according to the invention of the selective integrin receptor inhibitors as internal combination therapy of at least two integrin inhibitors are other combinations with conventional therapies such as radiotherapy, tumour vaccination, immunotherapy or chemotherapy. This combined internal and external therapeutic approach ought to increase the efficacy of the treatment further, in particular reduce the dosage of the toxic therapeutic agents and thus also reduce the dose-related side effects.

The invention further relates to pharmaceutical compositions comprising at least one compounds of the formula I and/or one of its physiologically acceptable salts or solvates, which are produced in particular by nonchemical means. It is possible for this purpose to convert the compounds of the formula I together with at least one solid, liquid and/or semiliquid carrier or excipient and, where appropriate, in combination with one or more other active ingredients into a suitable dosage form.

These compositions can be used as pharmaceuticals in human or veterinary medicine. Suitable carriers are inorganic or organic substances which are suitable for enteral (for example oral), parenteral or topical administration and which do not react with the novel compounds, for example water, vegetable oils, benzyl alcohols, alkylene glycols, polyethylene glycols, glycerol triacetate, gelatin, carbohydrates such as lactose or starch, magnesium stearate, talc, petrolatum. Used for oral administration are, in particular, tablets, pills, coated tablets, capsules, powders, granules, syrups, suspensions or drops, for rectal administration are suppositories, for parenteral administration are solutions, preferably oily or aqueous solutions, also suspensions, emulsions or implants, for topical administration are ointments, creams or dusting powders. The novel compounds can also be lyophilized, and the resulting lyophilisates can be used, for example, for producing products for injection. The stated compositions can be sterilized and/or comprise excipients such as lubricants, preservatives, stabilizers and/or wetting agents, emulsifiers, salts to influence the osmotic pressure, buffer substances, colourants, flavourings and/or a plurality of other active ingredients, for example one or more vitamins. The sprays which can be used for administration as spray for inhalation comprise the active ingredient either dissolved or suspended in a propellant gas or mixture of propellant gases (for examples $CO_2$ or chlorofluorocarbons). In this case, the active ingredient is preferably used in micronized form, it being possible for one or more additional physiologically tolerated solvents to be present, for example ethanol. Solutions for inhalation can be administered using conventional inhalers.

The compounds of the formula I and their physiologically acceptable salts or solvates can be used as integrin inhibitors for controlling diseases, in particular thromboses, myocardial infarct, coronary heart disease, arteriosclerosis, tumours, osteoporosis, inflammations and infections.

The compounds of the formula I according to claim 1 and/or their physiologically acceptable salts are also used for pathological processes which are maintained or propagated by angiogenesis, in particular tumours or rheumatoid arthritis.

Selected compounds of the formula I and/or their solvates, as described above, are used for controlling pathological processes influenced by the integrins $\alpha v\beta 3$ and/or $\alpha v\beta 5$ and $\alpha v\beta 6$, in particular cancer therapy, there being suppression on the one hand of angiogenesis with the blood vessels growing into the tumour through inhibition of the $\alpha v\beta 3$ integrin receptor and/or of the $\alpha v\beta 5$ integrin receptor, and on the other hand of tumour development through inhibition of the $\alpha v\beta 6$ integrin receptor.

In this case, the substances according to the invention are usually administered in analogy to the compounds described in WO 97/26250 or WO 97/24124, preferably in dosages between about 0.05 and 500 mg, in particular between 0.5 and 100 mg, per dose unit. The daily dose is preferably between about 0.01 and 2 mg/kg of body weight. The specific dose for each patient depends, however, on a wide variety of factors, for example on the efficacy of the specific compound employed, on the age, body weight, general state of health, sex, on the diet, on the time and mode of administration, on the rate of excretion, medicinal substance combination and severity of the particular disorder for which the therapy is applied. Parenteral administration is preferred.

The compounds of the formula I can also be used as integrin ligands for producing columns for affinity chromatography to prepare pure integrins.

The ligand, that is to say a compound of the formula I, is in this case covalently coupled via an anchor functionality, for example the carboxyl group, to a polymeric support.

Suitable polymeric support materials are the polymeric solid phases known per se in peptide chemistry, which preferably have hydrophilic properties, for example crosslinked polysaccharides such as cellulose, Sepharose or Sephadex$^R$, acrylamides, polymers based on polyethylene glycol, or Tentakel$^R$ polymers.

The materials for the affinity chromatography for purifying integrins are produced under conditions like those customary and known per se for condensing amino acids.

The compounds of the formula I contain one or more chiral centres and can therefore exist in racemic or in optically active form. Racemates which are obtained can be separated into the enantiomers mechanically or chemically by methods known per se. It is preferred to form diastereomers from the racemic mixture by reaction with an optically active resolving agent. Examples of suitable resolving agents are optically active acids such as the D and L forms of tartaric acid, diacetyltartaric acid, dibenzoyltartaric acid, mandelic acid, malic acid, lactic acid or the various optically active camphorsulfonic acids such as $\beta$-camphorsulfonic acid. It is also advantageous to separate the enantiomers using a column packed with an optically active resolving agent (for example dinitrobenzoylphenylglycine); an example of a suitable eluent is a hexane/isopropanol/acetonitrile mixture, for example in the ratio 82:15:3 by volume.

It is, of course, also possible to obtain optically active compounds of the formula I in the methods described above by using starting materials which are already optically active.

All temperatures herebefore and hereinafter are stated in ° C. In the following examples, "usual workup" means: water is added if necessary, the pH is adjusted to between 2 and 10 if necessary, depending on the constitution of the final product, extraction is carried out with ethyl acetate or dichloromethane, and the organic phase is separated off, dried over sodium sulfate, evaporated and purified by chromatography on silica gel, by preparation HPLC and/or by crystallization. The purified compounds are freeze dried where appropriate.

RT=retention time (in minutes) on HPLC in the following systems;
Column:
Lichrosorb RP-18 (5 $\mu$m) 250×4 mm;
Lichrosorb RP-18 (15 $\mu$m) 250×50 mm.
The eluents used are gradients of acetonitrile (B) with 0.1% TFA (trifluoroacetic acid) and water (A) with 0.1% TFA. The gradient is stated in percent acetonitrile by volume.

Preferred gradient: 5 min at 20% B and 55 min up to 90% B.

Detection at 225 nm.

The retention times labelled with * were measured with the gradient 5 min at 5% B and 40 min up to 80% B. The compounds purified by preparation HPLC are isolated as trifluoroacetates.

Mass spectrometry (MS) by FAB (fast atom bombardment): MS-FAB $(M+H)^+$.

EXAMPLE 1

(1) 10.5 g of 4-(trifluoromethoxy)benzaldehyde, 5.72 g of malonic acid, 8.5 g of ammonium acetate and 40 ml of ethanol are boiled under reflux for 8 hours and stirred at room temperature overnight. The cooled reaction mixture is then filtered with suction, washed with ethanol and ether and dried in air. 3-amino-3-(4-trifluoromethoxyphenyl) propionic acid is obtained, melting point 258–260°.

7.5 g of 3-amino-3-(4-trifluoromethoxyphenyl)propionic acid is activated with thionyl chloride (1.2 equivalent) and esterified with methanol at the boiling point under standard conditions. The usual workup results in methyl 3-amino-3-(4-trifluoromethoxyphenyl)propionate, FAB-MS $(M+H)^+$ 263.

(2) 0.364 g of [4-(pyridin-2-ylamino)butyrylamino]acetic acid [obtained from peptide coupling of 4-(pyridin-2-ylamino)butyric acid with glycine methyl ester in the presence of HOBT/TBTU and subsequent hydrolysis of the methyl ester, in each case under standard conditions] is dissolved in 30 ml of DMF, and 0.3 g of methyl 3-amino-3-(4-trifluoromethoxyphenyl)propionate is added, and the mixture is cooled to −30°. Addition of 0.321 g of TBTU and 0.045 g of HOBT is followed by neutralization with 0.22 ml of N-methylmorpholine (NMM). The reaction mixture is stirred at room temperature for 2 days. After removal of the solvent by distillation, the residue is taken up in ethyl acetate, washed with NaHCO$_3$ and saturated NaCl solution and further worked up as usual. Methyl 3-{2-[4-(4-methylpyridin-2-ylamino)butyrylamino]acetylamino}-3-(4-trifluoromethoxyphenyl)propionate is obtained, FAB-MS (M+H)$^+$ 497.

(3) 280 mg of methyl 3-{2-[4-(4-methylpyridin-2-ylamino)butyrylamino]acetylamino}-3-(4-trifluoromethoxyphenyl)propionate (crude material) are dissolved in 30 ml of dioxane, and 0.61 ml of NaOH (2 mol/l) is added. Stirring at room temperature overnight is followed by removal of the solvent by distillation and the usual workup. 3-{2-[4-(4-methylpyridin-2-ylamino)butyrylamino]acetylamino}-3-(4-trifluoromethoxyphenyl)propionic acid is obtained. If an excess of NaOH is used, the sodium salt of 3-{2-[4-(4-methylpyridin-2-ylamino)butyrylamino]acetylamino}-3-(4-trifluoromethoxyphenyl)propionic acid is obtained. Preparative HPLC results in 3-{2-[4-(4-methylpyridin-2-ylamino)butyrylamino]acetylamino}-3-(4-trifluoromethoxyphenyl)propionic acid trifluoroacetate, RT 24.93 min, FAB-MS (M+H)$^+$ 483.

EXAMPLE 2

(1) 0.06 mol of 2-nitrobenzaldehyde, 5.72 g of malonic acid, 8.5 g of ammonium acetate and 40 ml of ethanol are boiled under reflux for 8 hours and stirred at room temperature overnight. The cooled reaction mixture is then filtered with suction, washed with ethanol and ether and dried in air. 3-Amino-3-(2-nitrophenyl)propionic acid is obtained, melting point 222°. Subsequent esterification by activation with thionyl chloride and reaction with methanol under standard conditions produces methyl 3-amino-3-(2-nitrophenyl)propionate.

(2) Methyl 3-amino-3-(2-nitrophenyl)propionate is reacted in analogy to Example 1 (2) with BOC-protected glycine (BOC-Gly-OH). After the amino protective group BOC has been cleaved off under standard conditions, methyl 3-(2-aminoacetylamino)-3-(2-nitrophenyl)propionate hydrochloride is obtained, FAB-MS (M+H)$^+$ 317.

(3) 360 mg of methyl 3-(2-aminoacetylamino)-3-(2-nitrophenyl)propionate hydrochloride are dissolved in 35 ml of DMF, and 190 mg of 4-(4-methylpyridin-2-ylamino)butyric acid are added. After cooling the reaction mixture to 0°, 450 mg of TBTU and 63 mg of HOBt are added. It is neutralized with 0.15 ml of N-methylmorpholine and stirred at room temperature overnight. The solvent is distilled off, and the residue is mixed with 30 ml of ethyl acetate and washed with half-concentrated bicarbonate solution and saturated brine and worked up further as usual. Methyl 3-{2-[4-(4-methylpyridin-2-ylamino)butyrylamino]acetylamino}-3-(2-nitrophenyl)propionate is obtained.

(4) 280 mg of methyl 3-{2-[4-(4-methylpyridin-2-ylamino)butyrylamino]acetylamino}-3-(2-nitrophenyl)propionate (crude material) are dissolved in 30 ml of dioxane, and 0.61 ml of NaOH (2 mol/l) is added. Stirring at room temperature overnight is followed by removal of the solvent by distillation and the usual workup. 3-{2-[4-(4-methylpyridin-2-ylamino)butyrylamino]acetylamino}-3-(2-nitrophenyl)propionic acid is obtained. If an excess of NaOH is used, the sodium salt of 3-{2-[4-(4-methylpyridin-2-ylamino)butyrylamino]acetylamino}-3-(2-nitrophenyl) propionic acid is obtained. Preparative HPLC results in 3-{2-[4-(4-methylpyridin-2-ylamino)butyrylamino]acetylamino}-3-(2-nitrophenyl)propionic acid trifluoroacetate, RT 16.14 min, FAB-MS (M+H)$^+$ 444.

EXAMPLE 3

In analogy to Example 2, 4-(4-methylpyridin-2-ylamino)-butyric acid "AB" gives with methyl 3-(2-aminoacetylamino)-3-(3-trifluoromethoxyphenyl)propionate hydrochloride
  methyl 3-{2-[4-(4-methylpyridin-2-ylamino)butyrylamino]acetylamino}-3-(3-trifluoromethoxyphenyl)propionate;

with methyl 3-(2-aminoacetylamino)-3-(4-methyl-3-nitrophenyl)propionate hydrochloride
  methyl 3-{2-[4-(4-methylpyridin-2-ylamino)butyrylamino]acetylamino}-3-(4-methyl-3-nitrophenyl)propionate;

with methyl 3-(2-aminoacetylamino)-3-(3-nitrophenyl)propionate hydrochloride
  methyl 3-{2-[4-(4-methylpyridin-2-ylamino)butyrylamino]acetylamino}-3-(3-nitrophenyl)propionate, preparative HPLC results in methyl 3-(3-nitrophenyl)-3-{2-[4-(4-methylpyridin-2-ylamino)butyrylamino]acetylamino}propionate trifluoroacetate, RT* 19.09, FAB-MS (M+H)$^+$ 458 or with methyl 3-(2-aminoacetylamino)-3-(4-biphenyl)propionate hydrochloride
  methyl 3-{2-[4-(4-methylpyridin-2-ylamino)butyrylamino]acetylamino}-3-(4-biphenylyl)propionate.

EXAMPLE 4

Hydrolysis of the methyl esters of the compounds of Example 3 in analogy to Example 2 (4) results in 3-{2-[4-(4-methylpyridin-2-ylamino)butyrylamino]acetylamino}-3-(3-trifluoromethoxyphenyl)propionic acid; sodium salt of 3-{2-[4-(4-methylpyridin-2-ylamino)butyrylamino]acetylamino}-3-(3-trifluoromethoxyphenyl)propionic acid;

3-{2-[4-(4-methylpyridin-2-ylamino)butyrylamino]acetylamino}-3-(3-trifluoromethoxyphenyl)propionic acid trifluoroacetate; RT 24.40 min, FAB-MS (M+H)$^+$ 483;

3-(4-methyl-3-nitrophenyl)-3-{2-[4-(4-methylpyridin-2-ylamino)butyrylamino]acetylamino}propionic acid, 3-(4-methyl-3-nitrophenyl)-3-{2-[4-(4-methylpyridin-2-ylamino)butyrylamino]acetylamino}propionic acid sodium salt;

3-(4-methyl-3-nitrophenyl)-3-{2-[4-(4-methylpyridin-2-ylamino)butyrylamino]acetylamino}propionic acid trifluoroacetate, RT 19.18 min, FAB-MS (M+H)$^+$ 458;

3-{2-[4-(4-methylpyridin-2-ylamino)butyrylamino]acetylamino}-3-(3-nitrophenyl)propionic acid;

3-{2-[4-(4-methylpyridin-2-ylamino)butyrylamino]acetylamino}-3-(3-nitrophenyl)propionic acid sodium salt;

3-{2-[4-(4-methylpyridin-2-ylamino)butyrylamino]acetylamino}-3-(3-nitrophenyl)propionic acid trifluoroacetate, RT 17.68 min; FAB-MS (M+H)$^+$ 444 or 3-{2-[4-(4-methylpyridin-2-ylamino)butyrylamino]
acetylamino}-3-(4-biphenylyl)propionic acid,
3-{2-[4-(4-methylpyridin-2-ylamino)butyrylamino]
acetylamino}-3-(4-biphenylyl)propionic acid sodium salt,
3-{2-[4-(4-methylpyridin-2-ylamino)butyrylamino]
acetylamino}-3-(4-biphenylyl)propionic acid
trifluoroacetate, RT 25.65 min, FAB-MS (M+H)$^+$ 475.

EXAMPLE 5

In analogy to Example 2, 5-(4-methylpyridin-2-ylamino)
pentanoic acid "BC" gives
with methyl 3-(2-aminoacetylamino)-3-(4-trifluoromethoxyphenyl)propionate hydrochloride
methyl 3-{2-[5-(4-methylpyridin-2-ylamino)
pentanoylamino]acetylamino}-3-(4-trifluoromethoxyphenyl)propionate;
with methyl 3-(2-aminoacetylamino)-3-(3-trifluoromethoxyphenyl)propionate hydrochloride
methyl 3-{2-[5-(4-methylpyridin-2-ylamino)
pentanoylamino]acetylamino}-3-(3-trifluoromethoxyphenyl)propionate;
with methyl 3-(2-aminoacetylamino)-3-(4-methyl-3-nitrophenyl)propionate hydrochloride
methyl 3-(4-methyl-3-nitrophenyl)-3-{2-[5-(4-methylpyridin-2-ylamino)pentanoylamino]
acetylamino}propionate; HPLC results in methyl 3-(4-methyl-3-nitrophenyl)-3-{2-[5-(4-methylpyridin-2-ylamino)pentanoylamino]acetylamino}propionate, RT 23.81 min, FAB-MS (M+H)$^+$ 486;
with methyl 3-(2-aminoacetylamino)-3-(2-nitrophenyl)
propionate hydrochloride
methyl 3-{2-[5-(4-methylpyridin-2-ylamino)
pentanoylamino]acetylamino}-3-(2-nitrophenyl)
propionate;
with methyl 3-(2-aminoacetylamino)-3-(3-nitrophenyl)
propionate hydrochloride
methyl 3-(3-nitrophenyl)-3-{2-[5-(4-methylpyridin-2-ylamino)pentanoylamino]acetylamino}propionate;
with methyl 3-(2-aminoacetylamino)-3-(4-methyl-3-nitrophenyl)propionate hydrochloride
methyl 3-(4-methyl-3-nitrophenyl)-3-{2-[5-(4-methylpyridin-2-ylamino)pentanoylamino]
acetylamino}propionate;
with methyl 3-(2-aminoacetylamino)-3-(4-naphthalen-2-ylphenyl)propionate hydrochloride
methyl 3-(4-naphthalen-2-ylphenyl)-3-{2-[5-(4-methylpyridin-2-ylamino)pentanoylamino]
acetylamino}propionate;
with methyl 3-(2-aminoacetylamino)-3-(4-chloro-3-nitrophenyl)propionate hydrochloride
methyl 3-(4-chloro-3-nitrophenyl)-3-{2-[5-(4-methylpyridin-2-ylamino)pentanoylamino]
acetylamino}propionate or
with methyl 3-(2-aminoacetylamino)-3-(4-biphenylyl)
propionate hydrochloride
methyl 3-biphenyl-4-yl-3-{2-[5-methylpyridin-2-ylamino)pentanoylamino]acetylamino}propionate;
preparative HPLC results in methyl 3-biphenyl-4-yl-3-
{2-[5-(4-methylpyridin-2-ylamino)pentanoylamino]
acetylamino}propionate trifluoroacetate, RT 30.13 min,
FAB-MS (M+H)$^+$ 503.

EXAMPLE 6

Hydrolysis of the methyl esters of the compounds of
Example 5 in analogy to Example 2 (4) results in 3-{2-[5-(4-methylpyridin-2-ylamino)pentanoylamino]
acetylamino}-3-(4-trifluoromethoxyphenyl)propionic
acid,
3-{2-[5-(4-methylpyridin-2-ylamino)pentanoylamino]
acetylamino}-3-(4-trifluoromethoxyphenyl)propionic
acid sodium salt,
3-{2-[5-(4-methylpyridin-2-ylamino)pentanoylamino]
acetylamino}-3-(4-trifluoromethoxyphenyl)propionic
acid trifluoroacetate, RT 24.88 min, FAB-MS (M+H)$^+$ 497;
3-{2-[5-(4-methylpyridin-2-ylamino)pentanoylamino]
acetylamino}-3-(3-trifluoromethoxyphenyl)propionic
acid,
3-{2-[5-(4-methylpyridin-2-ylamino)pentanoylamino]
acetylamino}-3-(3-trifluoromethoxyphenyl)propionic
acid sodium salt,
3-{2-[5-(4-methylpyridin-2-ylamino)pentanoylamino]
acetylamino}-3-(3-trifluoromethoxyphenyl)propionic
acid trifluoroacetate, RT 24.61 min, FAB-MS (M+H)$^+$ 497;
3-(4-methyl-3-nitrophenyl)-3-{2-[5-(4-methylpyridin-2-ylamino)pentanoylamino]acetylamino}propionic acid,
3-(4-methyl-3-nitrophenyl)-3-{2-[5-(4-methylpyridin-2-ylamino)pentanoylamino]acetylamino}propionic acid
sodium salt,
3-(4-methyl-3-nitrophenyl)-3-{2-[5-(4-methylpyridin-2-ylamino)pentanoylamino]acetylamino}propionic acid
trifluoroacetate, RT 22.13 min, FAB-MS (M+H)$^+$ 472;
3-{2-[5-(4-methylpyridin-2-ylamino)pentanoylamino]
acetylamino}-3-(2-nitrophenyl)propionic acid,
3-{2-[5-(4-methylpyridin-2-ylamino)pentanoylamino]
acetylamino}-3-(2-nitrophenyl)propionic acid sodium
salt,
3-{2-[5-(4-methylpyridin-2-ylamino)pentanoylamino]
acetylamino}-3-(2-nitrophenyl)propionic acid
trifluoroacetate, RT 16.98 min, FAB-MS (M+H)$^+$ 458;
3-(3-nitrophenyl)-3-{2-[5-(4-methylpyridin-2-ylamino)
pentanoylamino]acetylamino}propionic acid,
3-(3-nitrophenyl)-3-{2-[5-(4-methylpyridin-2-ylamino)
pentanoylamino]acetylamino}propionic acid sodium salt,
3-(3-nitrophenyl)-3-{2-[5-(4-methylpyridin-2-ylamino)
pentanoylamino]acetylamino}propionic acid
trifluoroacetate, RT 17.29 min, FAB-MS (M+H)$^+$ 458;
3-(4-naphthalen-2-ylphenyl)-3-{2-[5-(4-methylpyridin-2-ylamino)pentanoylamino]acetylamino}propionic acid,
3-(4-naphthalen-2-ylphenyl)-3-{2-[5-(4-methylpyridin-2-ylamino)pentanoylamino]acetylamino}propionic acid
sodium salt,
3-(4-naphthalen-2-ylphenyl)-3-{2-[5-(4-methylpyridin-2-ylamino)pentanoylamino]acetylamino}propionic acid trifluoroacetate;
3-(4-chloro-3-nitrophenyl)-3-{2-[5-(4-methylpyridin-2-ylamino)pentanoylamino]acetylamino}propionic acid,
3-(4-chloro-3-nitrophenyl)-3-{2-[5-(4-methylpyridin-2-ylamino)pentanoylamino]acetylamino}propionic acid
sodium salt,
3-(4-chloro-3-nitrophenyl)-3-{2-[5-(4-methylpyridin-2-ylamino)pentanoylamino]acetylamino}propionic acid
trifluoroacetate, RT 22.34 min, FAB-MS (M+H)$^+$ 492 or
3-biphenyl-4-yl-3-{2-[5-(4-methylpyridin-2-ylamino)
pentanoylamino]acetylamino}propionic acid,
3-biphenyl-4-yl-3-{2-[5-(4-methylpyridin-2-ylamino)
pentanoylamino]acetylamino}propionic acid sodium salt,
3-biphenyl-4-yl-3-{2-[5-(4-methylpyridin-2-ylamino)
pentanoylamino]acetylamino}propionic acid
trifluoroacetate, RT 27.09 min, FAB-MS (M+H)$^+$ 489.

EXAMPLE 7

In analogy to Example 2, 4-(pyridin-2-ylamino)butyric acid "CD" gives with methyl 3-(2-aminoacetylamino)-3-(4-methyl-3-nitrophenyl)propionate hydrochloride methyl 3-(4-methyl-3-nitrophenyl)-3-{2-[4-(pyridin-2-ylamino)butyrylamino]acetylamino}propionate;

with methyl 3-(2-aminoacetylamino)-3-(2-nitrophenyl)propionate hydrochloride methyl 3-(2-nitrophenyl)-3-{2-[4-(pyridin-2-ylamino)butyrylamino]acetylamino}propionate or with methyl 3-(2-aminoacetylamino)-3-(4-biphenylyl)propionate hydrochloride methyl 3-{2-[4-(pyridin-2-ylamino)butyrylamino]acetylamino}-3-(4-biphenylyl)propionate.

EXAMPLE 8

Hydrolysis of the methyl esters of the compounds of Example 7 in an analogy to Example 2 (4) results in 3-(4-methyl-3-nitrophenyl)-3-{2-[4-(pyridin-2-ylamino)butyrylamino]acetylamino}propionic acid, 3-(4-methyl-3-nitrophenyl)-3-{2-[4-(pyridin-2-ylamino)butyrylamino]acetylamino}propionic acid sodium salt, 3-(4-methyl-3-nitrophenyl)-3-{2-[4-(pyridin-2-ylamino)butyrylamino]acetylamino}propionic acid trifluoroacetate, RT 19.12 min, FAB-MS (M+H)$^+$ 444;

3-(2-nitrophenyl)-3-{2-[4-(pyridin-2-ylamino)butyrylamino]acetylamino}propionic acid, 3-(2-nitrophenyl)-3-{2-[4-(pyridin-2-ylamino)butyrylamino]acetylamino}propionic acid sodium salt, 3-(2-nitrophenyl)-3-{2-[4-(pyridin-2-ylamino)butyrylamino]acetylamino}propionic acid trifluoroacetate, RT 12.42 min, FAB-MS (M+H)$^+$ 430 or 3-(biphenyl-4-yl)-3-{2-[4-(pyridin-2-ylamino)butyrylamino]acetylamino}propionic acid, 3-(biphenyl-4-yl)-3-{2-[4-(pyridin-2-ylamino)butyrylamino]acetylamino}propionic acid sodium salt, 3-(biphenyl-4-yl)-3-{2-[4-(pyridin-2-ylamino)butyrylamino]acetylamino}propionic acid trifluoroacetate, RT 25.20 min, FAB-MS (M+H)$^+$ 461.

EXAMPLE 9

In analogy to Example 2, 5-(pyridin-2-ylamino)pentanoic acid "DE" gives with methyl 3-(2-aminoacetylamino)-3-(4-methyl-3-nitrophenyl)propionate hydrochloride methyl 3-(4-methyl-3-nitrophenyl)-3-{2-[5-pyridin-2-ylamino)pentanoylamino]acetylamino}propionate;

with methyl 3-(2-aminoacetylamino)-3-(2-nitrophenyl)propionate hydrochloride methyl 3-(2-nitrophenyl)-3-{2-[5-(pyridin-2-ylamino)pentanoylamino]acetylamino}propionate or with methyl 3-(2-aminoacetylamino)-3-(4-biphenylyl)propionate hydrochloride methyl 3-biphenyl-4-yl-3-{2-[5-(pyridin-2-ylamino)pentanoylamino]acetylamino}propionate, preparative HPLC results in methyl 3-biphenyl-4-yl-3-{2-[5-(pyridin-2-ylamino)pentanoylamino]acetylamino}propionate trifluoroacetate, RT 28.88 min, FAB-MS (M+H)$^+$ 489.

EXAMPLE 10

Hydrolysis of the methyl esters of the compounds of Example 9 in analogy to Example 2 (4) results in 3-(4-methyl-3-nitrophenyl)-3-{2-[5-(pyridin-2-ylamino)pentanoylamino]acetylamino}propionic acid, 3-(4-methyl-3-nitrophenyl)-3-{2-[5-(pyridin-2-ylamino)pentanoylamino]acetylamino}propionic acid sodium salt, 3-(4-methyl-3-nitrophenyl)-3-{2-[5-(pyridin-2-ylamino)pentanoylamino]acetylamino}propionic acid trifluoroacetate, RT 19.78 min, FAB-MS (M+H)$^+$ 458;

3-(2-nitrophenyl)-3-{2-[5-(pyridin-2-ylamino)pentanoylamino]acetylamino}propionic acid, 3-(2-nitrophenyl)-3-{2-[5-(pyridin-2-ylamino)pentanoylamino]acetylamino}propionic acid sodium salt, 3-(2-nitrophenyl)-3-{2-[5-(pyridin-2-ylamino)pentanoylamino]acetylamino}propionic acid trifluoroacetate, RT 12.80 min, FAB-MS (M+H)$^+$ 444 or 3-biphenyl-4-yl-3-{2-[5-(pyridin-2-ylamino)pentanoylamino]acetylamino}propionic acid, 3-biphenyl-4-yl-3-{2-[5-(pyridin-2-ylamino)pentanoylamino]acetylamino}propionic acid sodium salt, 3-biphenyl-4-yl-3-{2-[5-(pyridin-2-ylamino)pentanoylamino]acetylamino}propionic acid trifluoroacetate, RT 25.84 min, FAB-MS (M+H)$^+$ 475.

EXAMPLE 11

In analogy to Example 2, 4-(6-methylpyridin-2-ylamino)butyric acid "EF" gives with methyl 3-(2-aminoacetylamino)-3-(4-methyl-3-nitrophenyl)propionate hydrochloride methyl 3-(4-methyl-3-nitrophenyl)-3-{2-[4-(6-methylpyridin-2-ylamino)butyrylamino]acetylamino}propionate.

In analogy to Example 2, 5-(6-methylpyridin-2-ylamino)pentanoic acid "FG" gives with methyl 3-(2-aminoacetylamino)-3-(4-methyl-3-nitrophenyl)propionate hydrochloride methyl 3-(4-methyl-3-nitrophenyl)-3-{2-[5-(6-methylpyridin-2-ylamino)pentanoylamino]acetylamino}propionate.

EXAMPLE 12

Hydrolysis of the methyl esters of the compounds of Example 11 in analogy to Example 2 (4) results in 3-(4-methyl-3-nitrophenyl)-3-{2-[4-(6-methylpyridin-2-ylamino)butyrylamino]acetylamino}propionic acid, 3-(4-methyl-3-nitrophenyl)-3-{2-[4-(6-methylpyridin-2-ylamino)butyrylamino]acetylamino}propionic acid sodium salt, 3-(4-methyl-3-nitrophenyl)-3-{2-[4-(6-methylpyridin-2-ylamino)butyrylamino]acetylamino}propionic acid trifluoroacetate or 3-(4-methyl-3-nitrophenyl)-3-{2-[5-(6-methylpyridin-2-ylamino)pentanoylamino]acetylamino}propionic acid, 3-(4-methyl-3-nitrophenyl)-3-{2-[5-(6-methylpyridin-2-ylamino)pentanoylamino]acetylamino}propionic acid sodium salt, 3-(4-methyl-3-nitrophenyl)-3-{2-[5-(6-methylpyridin-2-ylamino)pentanoylamino]acetylamino}propionic acid trifluoroacetate.

EXAMPLE 13

In analogy to Example 2, 4-(pyrimidin-2-ylamino)butyric acid "GH" gives with methyl 3-(2-aminoacetylamino)-3-(4-methyl-3-nitrophenyl)propionate hydrochloride methyl 3-(4-methyl-3-nitrophenyl)-3-{2-[4-(pyrimidin-2-ylamino)butyrylamino]acetylamino}propionate or with methyl 3-(2-aminoacetylamino)-3-(4-biphenylyl) propionate hydrochloride
methyl 3-{2-[4-(pyrimidin-2-ylamino)butyrylamino] acetylamino}-3-(4-biphenylyl)propionate.
In analogy to Example 2, 5-(pyrimidin-2-ylamino) pentanoic acid "HK" gives
with methyl 3-(2-aminoacetylamino)-3-(4-methyl-3-nitrophenyl)propionate hydrochloride
methyl 3-(4-methyl-3-nitrophenyl)-3-{2-[5-(pyrimidin-2-ylamino)pentanoylamino]acetylamino}propionate or
with methyl 3-(2-aminoacetylamino)-3-(4-biphenylyl) propionate hydrochloride
methyl 3-{2-[5-(pyrimidin-2-ylamino)pentanoylamino] acetylamino}-3-(4-biphenylyl)propionate.

EXAMPLE 14

Hydrolysis of the methyl esters of the compounds of Example 13 in analogy to Example 2 (4) results in
3-(4-methyl-3-nitrophenyl)-3-{2-[4-(pyrimidin-2-ylamino) butyrylamino]acetylamino}propionic acid,
3-(4-methyl-3-nitrophenyl)-3-{2-[4-(pyrimidin-2-ylamino) butyrylamino]acetylamino}propionic acid sodium salt,
3-(4-methyl-3-nitrophenyl)-3-{2-[4-(pyrimidin-2-ylamino) butyrylamino]acetylamino}propionic acid trifluoroacetate, RT 16.33 min, FAB-MS (M+H)$^+$ 445;
3-biphenyl-4-yl-3-{2-[4-(pyrimidin-2-ylamino) butyrylamino]acetylamino}propionic acid,
3-biphenyl-4-yl-3-{2-[4-(pyrimidin-2-ylamino) butyrylamino]acetylamino}propionic acid sodium salt,
3-biphenyl-4-yl-3-{2-[4-(pyrimidin-2-ylamino) butyrylamino]acetylamino}propionic acid trifluoroacetate, RT 24.45 min, FAB-MS (M+H)$^+$ 462;
3-(4-methyl-3-nitrophenyl)-3-{2-[5-(pyrimidin-2-ylamino) pentanoylamino]acetylamino}propionic acid,
3-(4-methyl-3-nitrophenyl)-3-{2-[5-(pyrimidin-2-ylamino) pentanoylamino]acetylamino}propionic acid sodium salt,
3-(4-methyl-3-nitrophenyl)-3-{2-[5-(pyrimidin-2-ylamino) pentanoylamino]acetylamino}propionic acid trifluoroacetate or
3-biphenyl-4-yl-3-{2-[5-(pyrimidin-2-ylamino) pentanoylamino]acetylamino}propionic acid,
3-biphenyl-4-yl-3-{2-[5-(pyrimidin-2-ylamino) pentanoylamino]acetylamino}propionic acid sodium salt,
3-biphenyl-4-yl-3-{2-[5-(pyrimidin-2-ylamino) pentanoylamino]acetylamino}propionic acid trifluoroacetate.

EXAMPLE 15

In analogy to Example 2, 4-(6-methylpyridin-2-ylamino) butyric acid "EF" gives
with methyl 3-(2-aminoacetylamino)-3-(4-methyl-3-nitrophenyl)propionate hydrochloride
methyl 3-(4-methyl-3-nitrophenyl)-3-{2-[4-(6-methylpyridin-2-ylamino)butyrylamino] acetylamino}propionate.
Hydrolysis of the methyl ester in analogy to Example 2 (4) results in
3-(4-methyl-3-nitrophenyl)-3-{2-[4-(6-methylpyridin-2-ylamino)butyrylamino]acetylamino}propionic acid,
3-(4-methyl-3-nitrophenyl)-3-{2-[4-(6-methylpyridin-2-ylamino)butyrylamino]acetylamino}propionic acid sodium salt;
3-(4-methyl-3-nitrophenyl)-3-{2-[4-(6-methylpyridin-2-ylamino)butyrylamino]acetylamino}propionic acid trifluoroacetate; RT 20.10 min, FAB-MS (M+H)$^+$ 458.

EXAMPLE 16

In analogy to Example 2, 6-(4-methylpyridin-2-ylamino) hexanoic acid "KL" gives
with methyl 3-(2-aminoacetylamino)-3-(4-methyl-3-nitrophenyl)propionate hydrochloride
methyl 3-(4-methyl-3-nitrophenyl)-3-{2-[6-(4-methylpyridin-2-ylamino)hexanoylamino] acetylamino}propionate;
with methyl 3-(2-aminoacetylamino)-3-(3-nitrophenyl) propionate hydrochloride
methyl 3-(3-nitrophenyl)-3-{2-[6-(4-methylpyridin-2-ylamino)hexanoylamino]acetylamino}propionate or
with methyl 3-(2-aminoacetylamino)-3-(4-chloro-3-nitrophenyl)propionate hydrochloride
methyl 3-(4-chloro-3-nitrophenyl)-3-{2-[6-(4-methylylpyridin-2-ylamino)hexanoylamino] acetylamino}propionate.
Hydrolysis of the abovementioned methyl esters in analogy to Example 2 (4) results in
3-(4-methyl-3-nitrophenyl)-3-{2-[6-(4-methylpyridin-2-ylamino)hexanoylamino]acetylamino}propionic acid,
3-(4-methyl-3-nitrophenyl)-3-{2-[6-(4-methylpyridin-2-ylamino)hexanoylamino]acetylamino}propionic acid sodium salt;
3-(4-methyl-3-nitrophenyl)-3-{2-[6-(4-methylpyridin-2-ylamino)hexanoylamino]acetylamino}propionic acid trifluoroacetate, RT 22.10 min, FAB-MS (M+H)$^+$ 468;
3-{2-[6-(4-methylpyridin-2-ylamino)hexanoylamino] acetylamino}-3-(3-nitrophenyl)propionic acid,
3-{2-[6-(4-methylpyridin-2-ylamino)hexanoylamino] acetylamino}-3-(3-nitrophenyl)propionic acid sodium salt,
3-{2-[6-(4-methylpyridin-2-ylamino)hexanoylamino] acetylamino}-3-(3-nitrophenyl)propionic acid trifluoroacetate, RT* 18.27 min, FAB-MS (M+H)$^+$ 472 or
3-(4-chloro-3-nitrophenyl)-3-{2-[6-(4-methylpyridin-2-ylamino)hexanoylamino]acetylamino}propionic acid,
3-(4-chloro-3-nitrophenyl)-3-{2-[6-(4-methylpyridin-2-ylamino)hexanoylamino]acetylamino}propionic acid sodium salt,
3-(4-chloro-3-nitrophenyl)-3-{2-[6-(4-methylpyridin-2-ylamino)hexanoylamino]acetylamino}propionic acid trifluoroacetate, RT 23.33 min, FAB-MS (M+H)$^+$ 506.

EXAMPLE 17

In analogy to Example 2, 7-(4-methylpyridin-2-ylamino) hexanoic acid "LM" gives
with methyl 3-(2-aminoacetylamino)-3-(4-nitrophenyl) propionate hydrochloride
methyl 3-{2-[7-(4-methylpyridin-2-ylmaino) heptanoylamino]acetylamino}-3-(3-nitrophenyl) propionate.
Hydrolysis of the methyl ester in analogy to Example 2 (4) results in
3-{2-[7-(4-methylpyridin-2-ylmaino)heptanoylamino] acetylamino}-3-(3-nitrophenyl)propionate acid,
3-{2-[7-(4-methylpyridin-2-ylmaino)heptanoylamino] acetylamino}-3-(3-nitrophenyl)propionate acid sodium salt,
3-{2-[7-(4-methylpyridin-2-ylmaino)heptanoylamino] acetylamino}-3-(3-nitrophenyl)propionate acid trifluoroacetate, RT 20.98 min, FAB-MS (M+H)$^+$ 486.

EXAMPLE 18

In analogy to Example 2, 5-(pyridin-2-ylamino)pentanoic acid "DE" gives with methyl 3-(2-aminoacetylamino)-3-(3-nitrophenyl)propionate hydrochloride
    methyl 3-(3-nitrophenyl)-3-{2-[5-(pyridin-2-ylamino)pentanoylamino]acetylamino}propionate;

with methyl 3-(2-aminoacetylamino)-3-(4-chloro-3-nitrophenyl)propionate hydrochloride
    methyl 3-(4-chloro-3-nitrophenyl)-3-{2-[5-(pyridin-2-ylamino)pentanoylamino]acetylamino}propionate;

with methyl 3-(2-aminoacetylamino)-3-(4'-fluorobiphenyl-4-yl)propionate hydrochloride
    methyl 3-(4'-fluorobiphenyl-4-yl)-3-{2-[5-(pyridin-2-ylamino)pentanoylamino]acetylamino}propionate;

with methyl 3-(2-aminoacetylamino)-3-(4'-fluorobiphenyl-3-yl)propionate hydrochloride
methyl 3-(4'-fluorobiphenyl-3-yl)-3-{2-[5-(pyridin-2-ylamino)pentanoylamino]acetylamino}propionate;

with methyl 3-(2-aminoacetylamino)-3-(3'-fluorobiphenyl-4-yl)propionate hydrochloride
    methyl 3-(3'-fluorobiphenyl-4-yl)-3-{2-[5-(pyridin-2-ylamino)pentanoylamino]acetylamino}propionate;

with methyl 3-(2-aminoacetylamino)-3-(2'-fluorobiphenyl-4-yl)propionate hydrochloride
    methyl 3-(2'-fluorobiphenyl-4-yl)-3-{2-[5-(pyridin-2-ylamino)pentanoylamino]acetylamino}propionate;

with methyl 3-(2-aminoacetylamino)-3-(4'-chlorobiphenyl-4-yl)propionate hydrochloride
    methyl 3-(4'-fluorobiphenyl-4-yl)-3-{2-[5-(pyridin-2-ylamino)pentanoylamino]acetylamino}propionate;

with methyl 3-(2-aminoacetylamino)-3-(3'-chlorobiphenyl-4-yl)propionate hydrochloride
    methyl 3-(3'-chlorobiphenyl-4-yl)-3-{2-[5-(pyridin-2-ylamino)pentanoylamino]acetylamino}propionate;

with methyl 3-(2-aminoacetylamino)-3-(4'-chlorobiphenyl-4-yl)propionate hydrochloride
    methyl 3-(4'-methylbiphenyl-4-yl)-3-{2-[5-(pyridin-2-ylamino)pentanoylamino]acetylamino}propionate;

with methyl 3-(2-aminoacetylamino)-3-[4'-trifluoromethyl)biphenyl-4-yl]propionate hydrochloride
    methyl 3-[4'-(trifluoromethyl)biphenyl-4-yl]-3-{2-[5-(pyridin-2-ylamino-pentanoylamino]acetylamino}propionate;

with methyl 3-(2-aminoacetylamino)-3-(3'-chloro-4'-fluorobiphenyl-4-yl)propionate hydrochloride
    methyl 3-(3'-chloro-4'-fluorobiphenyl-4-yl)-3-{2-[5-(pyridin-2-ylamino)petanoylamino]acetylamino}propionate;

with methyl 3-(2-aminoacetylamino)-3-(4-naphthalen-1-ylphenyl)propionate hydrochloride
    methyl 3-(4-naphthalen-1-ylphenyl)-3-{2-[5-(pyridin-2-ylamino)pentanoylamino]acetylamino}propionate;

with methyl 3-(2-aminoacetylamino)-3-(4-naphthalen-2-ylphenyl)propionate hydrochloride
    methyl 3-(4-naphthalen-1-ylphenyl)-3-{2-[5-(pyridin-2-ylamino)pentanoylamino]acetylamino}propionate or with methyl 3-(2-aminoacetylamino)-3-(4'-fluoro-2-hydroxybiphenyl-4-yl)propionate hydrochloride
    methyl 3-(4'-fluoro-2-hydroxybiphenyl-4-yl)-3-{2-[5-(pyridin-2-ylamino)pentanoylamino]acetylamino}propionate.

EXAMPLE 19

Hydrolysis of the methyl esters of the compounds of Example 18 in analogy to Example 2 (4) results in 3-(3-nitrophenyl)-3-{2-[5-(pyridin-2-ylamino)pentanoylamino]acetylamino]propionic acid,
3-(3-nitrophenyl)-3-{2-[5-(pyridin-2-ylamino)pentanoylamino]acetylamino]propionic acid sodium salt,
3-(3-nitrophenyl)-3-{2-[5-(pyridin-2-ylamino)pentanoylamino}acetylamino]propionic acid trifluoroacetate, RT* 16.07 min, FAB-MS (M+H)$^+$ 444;

3-(4-chloro-3-nitrophenyl)-3-{2-[5-(pyridin-2-ylamino)-pentanoylamino}acetylamino]propionic acid,
3-(4-chloro-3-nitrophenyl)-3-{2-[5-(pyridin-2-ylamino)-pentanoylamino}acetylamino]propionic acid sodium salt,
3-(4-chloro-3-nitrophenyl)-3-{2-[5-(pyridin-2-ylamino)-pentanoylamino]acetylamino}propionic acid trifluoroacetate, RT* 18.67 min, FAB-MS (M+H)$^+$ 478;

3-(4'-fluorobiphenyl-4-yl)-3-{2-[5-(pyridin-2-ylamino)-pentanoylamino]acetylamino}propionic acid,
3-(4'-fluorobiphenyl-4-yl)-3-{2-[5-(pyridin-2-ylamino)-pentanoylamino]acetylamino}propionic acid sodium salt,
3-(4'-fluorobiphenyl-4-yl)-3-{2-[5-(pyridin-2-ylamino)-pentanoylamino]acetylamino}propionic acid trifluoroacetate, RT* 24.66 min, FAB-MS (M+H)$^+$ 493;

3-(4'-fluorobiphenyl-3-yl)-3-{2-[5-(pyridin-2-ylamino)-pentanoylamino]acetylamino}propionic acid,
3-(4'-fluorobiphenyl-3-yl)-3-{2-[5-(pyridin-2-ylamino)-pentanoylamino]acetylamino}propionic acid sodium salt,
3-(4'-fluorobiphenyl-3-yl)-3-{2-[5-(pyridin-2-ylamino)-pentanoylamino]acetylamino}propionic acid trifluoroacetate, RT* 25.36 min, FAB-MS (M+H)$^+$ 493;

3-(3'-fluorobiphenyl-4-yl)-3-{2-[5-(pyridin-2-ylamino)-pentanoylamino]acetylamino}propionic acid,
3-(3'-fluorobiphenyl-4-yl)-3-{2-[5-(pyridin-2-ylamino)-pentanoylamino]acetylamino}propionic acid sodium salt,
3-(3'-fluorobiphenyl-4-yl)-3-{2-[5-(pyridin-2-ylamino)-pentanoylamino]acetylamino}propionic acid trifluoroacetate, FAB-MS (M+H)$^+$ 493;

3-(2'-fluorobiphenyl-4-yl)-3-{2-[5-(pyridin-2-ylamino)-pentanoylamino]acetylamino}propionic acid,
3-(2'-fluorobiphenyl-4-yl)-3-{2-[5-(pyridin-2-ylamino)-pentanoylamino]acetylamino}propionic acid sodium salt,
3-(2'-fluorobiphenyl-4-yl)-3-{2-[5-(pyridin-2-ylamino)-pentanoylamino]acetylamino}propionic acid trifluoroacetate, FAB-MS (M+H)$^+$ 493:

3-(4'-chlorobiphenyl-4-yl)-3-{2-[5-(pyridin-2-ylamino)-pentanoylamino]acetylamino}propionic acid,
3-(4'-chlorobiphenyl-4-yl)-3-{2-[5-(pyridin-2-ylamino)-pentanoylamino]acetylamino}propionic acid sodium salt,
3-(4'-chlorobiphenyl-4-yl)-3-{2-[5-(pyridin-2-ylamino)-pentanoylamino]acetylamino}propionic acid trifluoroacetate, FAB-MS (M+H)$^+$ 510;

3-(3'-chlorobiphenyl-4-yl)-3-{2-[5-(pyridin-2-ylamino)-pentanoylamino]acetylamino}propionic acid,
3-(3'-chlorobiphenyl-4-yl)-3-{2-[5-(pyridin-2-ylamino)-pentanoylamino]acetylamino}propionic acid sodium salt,
3-(3'-chlorobiphenyl-4-yl)-3-{2-[5-(pyridin-2-ylamino)-pentanoylamino]acetylamino}propionic acid trifluoroacetate, FAB-MS (M+H)$^+$ 510;

3-(4'-methylbiphenyl-4-yl)-3-{2-[5-(pyridin-2-ylamino)-pentanoylamino]acetylamino}propionic acid,
3-(4'-methylbiphenyl-4-yl)-3-{2-[5-(pyridin-2-ylamino)-pentanoylamino]acetylamino}propionic acid sodium salt, 3-(4'-methylbiphenyl-4-yl)-3-{2-[5-(pyridin-2-ylamino)-pentanoylamino]acetylamino}propionic acid trifluoroacetate, FAB-MS (M+H)+ 489;

3-[4'-(trifluoromethyl)biphenyl-4-yl]-3-{2-[5-(pyridin-2-ylamino)pentanoylamino]acetylamino}propionic acid,
3-[4'-(trifluoromethyl)biphenyl-4-yl]-3-{2-[5-(pyridin-2-ylamino)pentanoylamino]acetylamino}propionic acid sodium salt,
3-[4'-(trifluoromethyl)biphenyl-4-yl]-3-{2-[5-(pyridin-2-ylamino)pentanoylamino]acetylamino}propionic acid trifluoroacetate, FAB-MS (M+H)+ 543;

3-(3'-chloro-4'-fluorobiphenyl-4-yl)-3-{2-[5-(pyridin-2-ylamino)pentanoylamino]acetylamino}propionic acid,
3-(3'-chloro-4'-fluorobiphenyl-4-yl)-3-{2-[5-(pyridin-2-ylamino)pentanoylamino]acetylamino}propionic acid sodium salt,
3-(3-chloro-4'-fluorobiphenyl-4-yl)-3-{2-[5-(pyridin-2-ylamino)pentanoylamino]acetylamino}propionic acid trifluoroacetate, FAB-MS (M+H)+ 527;

3-(4-naphthalen-1-ylphenyl)-3-{2-[5-(pyridin-2-ylamino)pentanoylamino]acetylamino}propionic acid,
3-(4-naphthalen-1-ylphenyl)-3-{2-[5-(pyridin-2-ylamino)pentanoylamino]acetylamino}propionic acid sodium salt,
3-(4-naphthalen-1-ylphenyl)-3-{2-[5-(pyridin-2-ylamino)pentanoylamino]acetylamino}propionic acid trifluoroacetate, RT* 24.91 min, FAB-MS (M+H)+ 525;

3-(4-naphthalen-2-ylphenyl)-3-{2-[5-(pyridin-2-ylamino)pentanoylamino]acetylamino}propionic acid,
3-(4-naphthalen-2-ylphenyl)-3-{2-[5-(pyridin-2-ylamino)pentanoylamino]acetylamino}propionic acid sodium salt,
3-(4-naphthalen-2-ylphenyl)-3-{2-[5-(pyridin-2-ylamino)pentanoylamino]acetylamino}propionic acid trifluoroacetate or 3-(4'-fluoro-2-hydroxybiphenyl-4-yl)-3-{2-[5-(pyridin-2-ylamino)pentanoylamino]acetylamino}propionic acid,
3-(4'-fluoro-2-hydroxybiphenyl-4-yl)-3-{2-[5-(pyridin-2-ylamino)pentanoylamino]acetylamino}propionic acid sodium salt,
3-(4'-fluoro-2-hydroxybiphenyl-4-yl)-3-{2-[5-(pyridin-2-ylamino)pentanoylamino]acetylamino}propionic acid trifluoroacetate.

EXAMPLE 20

In analogy to Example 2, 4-(pyridin-2-ylamino)butyric acid "CD" gives
with methyl 3-(2-aminoacetylamino)-3-(3-nitrophenyl)-propionate hydrochloride
    methyl 3-(3-nitrophenyl)-3-{2-[4-(pyridin-2-ylamino)butyrylamino]acetylamino}propionate;
with methyl 3-(2-aminoacetylamino)-3-(4-chloro-3-nitrophenyl)propionate hydrochloride
    methyl 3-(4-chloro-3-nitrophenyl)-3-{2-[4-(pyridin-2-ylamino)butyrylamino]acetylamino}propionate;
with methyl 3-(2-aminoacetylamino)-3-(4'-fluorobiphenyl-4-yl)propionate hydrochloride
    methyl 3-(4'-fluorobiphenyl-4-yl)-3-{2-[4-(pyridin-2-ylamino)butyrylamino]acetylamino}propionate;
with methyl 3-(2-aminoacetylamino)-3-(4'-fluorobiphenyl-3-yl)propionate hydrochloride
    methyl (3-(4'-fluorobiphenyl-3-yl)-3-{2-[4-(pyridin-2-ylamino)butyrylamino]acetylamino}propionate;
with methyl 3-(2-aminoacetylamino)-3-(4-naphthalen-1-ylphenyl)propionate hydrochloride
    methyl 3-(4-naphthalen-1-ylphenyl)-3-{2-[4-(pyridin-2-ylamino)butyrylamino]acetylamino}propionate;
with methyl 3-(2-aminoacetylamino)-3-(2-hydroxy-4-naphthalen-1-ylphenyl)propionate hydrochloride
    methyl 3-(2-hydroxyl-4-naphthalen-1-ylphenyl)-3-{2-[4-(pyridin-2-ylamino)butyrylamino]acetylamino}propionate or
with methyl 3-(2-aminoacetylamino)-3-(2-hydroxybiphenyl-4-yl)propionate hydrochloride
    methyl 3-(2-hydroxylbiphenyl-4-yl)-3-{2-[4-(pyridin-2-ylamino)butyrylamino]acetylamino}propionate;

EXAMPLE 21

Hydrolysis of the methyl esters of the compounds of Example 20 in analogy to Example 2 (4) results in
3-(3-nitrophenyl)-3-{2-[4-(pyridin-2-ylamino)butyrylamino]acetylamino}propionic acid,
3-(3-nitrophenyl)-3-{2-[4-(pyridin-2-ylamino)butyrylamino]acetylamino}propionic acid sodium salt,
3-(3-nitrophenyl)-3-{2-[4-(pyridin-2-ylamino)butyrylamino]acetylamino}propionic acid trifluoroacetate, RT* 15.50, FAB-MS (M+H)+ 430;

3-(4-chloro-3-nitrophenyl)-3-{2-[4-(pyridin-2-ylamino)butyrylamino]acetylamino}propionic acid,
3-(4-chloro-3-nitrophenyl)-3-{2-[4-(pyridin-2-ylamino)butyrylamino]acetylamino}propionic acid sodium salt,
3-(4-chloro-3-nitrophenyl)-3-{2-[4-(pyridin-2-ylamino)butyrylamino]acetylamino}propionic acid trifluoroacetate, RT* 18.31, FAB-MS (M+H)+ 464;

3-(4'-fluorobiphenyl-4-yl)-3-{2-[4-(pyridin-2-ylamino)butyrylamino]acetylamino}propionic acid,
3-(4'-fluorobiphenyl-4-yl)-3-{2-[4-(pyridin-2-ylamino)butyrylamino]acetylamino}propionic acid sodium salt,
3-(4'-fluorobiphenyl-4-yl)-3-{2-[4-(pyridin-2-ylamino)butyrylamino]acetylamino}propionic acid trifluoroacetate, RT 24.53, FAB-MS (M+H)+ 479;

3-(4'-fluorobiphenyl-3-yl)-3-{2-[4-(pyridin-2-ylamino)butyrylamino]acetylamino}propionic acid,
3-(4'-fluorobiphenyl-3-yl)-3-{2-[4-(pyridin-2-ylamino)butyrylamino]acetylamino}propionic acid sodium salt,
3-(4'-fluorobiphenyl-3-yl)-3-{2-[4-(pyridin-2-ylamino)butyrylamino]acetylamino}propionic acid trifluoroacetate, RT 25.06, FAB-MS (M+H)+ 479;

3-(4-naphthalen-1-ylphenyl)-3-{2-[4-(pyridin-2-ylamino)butyrylamino]acetylamino}propionic acid,
3-(4-naphthalen-1-ylphenyl)-3-{2-[4-(pyridin-2-ylamino)butyrylamino]acetylamino}propionic acid sodium salt,
3-(4-naphthalen-1-ylphenyl)-3-{2-[4-(pyridin-2-ylamino)butyrylamino]acetylamino}propionic acid trifluoroacetate, RT* 24.80, FAB-MS (M+H)+ 511;

3-(4-naphthalen-1-yl-2-hydroxyphenyl)-3-{2-[4-(pyridin-2-ylamino)butyrylamino]acetylamino}propionic acid,
3-(4-naphthalen-1-yl-2-hydroxyphenyl)-3-{2-[4-(pyridin-2-ylamino)butyrylamino]acetylamino}propionic acid sodium salt,
3-(4-naphthalen-1-yl-2-hydroxyphenyl)-3-{2-[4-(pyridin-2-ylamino)butyrylamino]acetylamino}propionic acid trifluoroacetate or 3-(2-hydroxybiphenyl-4-yl)-3-{2-[4-(pyridin-2-ylamino)butyrylamino]acetylamino}propionic acid,
3-(2-hydroxybiphenyl-4-yl)-3-{2-[4-(pyridin-2-ylamino)butyrylamino]acetylamino}propionic acid sodium salt,
3-(2-hydroxybiphenyl-4-yl)-3-{2-[4-(pyridin-2-ylamino)butyrylamino]acetylamino}propionic acid trifluoroacetate.

EXAMPLE 22

In analogy to Example 2, 4-(4-methylpyridin-2-ylamino)butyric acid "AB" gives
with methyl 3-(2-aminoacetylamino)-3-(4-nitrophenyl)propionate hydrochloride
  methyl 3-{2-[4-(4-methylpyridin-2-ylamino)butyrylamino]acetylamino}-3-(4-nitrophenyl)propionate;
with methyl 3-(2-aminoacetylamino)-3-(3-nitro-2-hydroxyphenyl)propionate hydrochloride
  methyl 3-{2-[4-(4-methylpyridin-2-ylamino)butyrylamino]acetylamino}-3-(3-nitro-2-hydroxyphenyl)propionate;
with methyl 3-(2-aminoacetylamino)-3-(4-chloro-3-nitrophenyl)propionate hydrochloride
  methyl 3-{2-[4-(4-methylpyridin-2-ylamino)butyrylamino]acetylamino}-3 -(4-chloro-3-nitrophenyl)propionate;
with methyl 3-(2-aminoacetylamino)-3-(4'-fluorobiphenyl-3-yl)propionate hydrochloride
  methyl 3-{2-[4-(4-methylpyridin-2-ylamino)butyrylamino]acetylamino}-3-(4'-fluorobiphenyl-3-yl)propionate;
with methyl 3-(2-aminoacetylamino)-3-(4'-fluorobiphenyl-4-yl)propionate hydrochloride
  methyl 3-{2-[4-(4-methylpyridin-2-ylamino)butyrylamino]acetylamino}-3-(4'-fluorobiphenyl-4-yl)propionate;
with methyl 3-(2-aminoacetylamino)-3-(4-naphthalen-1-ylphenyl)propionate hydrochloride
  methyl 3-{2-[4-(4-methylpyridin-2-ylamino)butyrylamino]acetylamino}-3-(4-naphthalen-1-ylphenyl)propionate;
with methyl 3-(2-aminoacetylamino)-3-(4-naphthalen-1-yl-2-hydroxyphenyl)propionate hydrochloride
  methyl 3-{2-[4-(4-methylpyridin-2-ylamino)butyrylamino]acetylamino}-3-(4-naphthalen-1-yl-2-hydroxyphenyl)propionate;
with methyl 3-(2-aminoacetylamino)-3-(5-bromo-2-hydroxy-3-nitrophenyl)propionate hydrochloride
  methyl 3-{2-[4-(4-methylpyridin-2-ylamino)butyrylamino]acetylamino}-3-(5-bromo-2-hydroxy-3-nitrophenyl)propionate;
with methyl 3-(2-aminoacetylamino)-3-(4-naphthalen-2-ylphenyl)propionate hydrochloride
  methyl 3-{2-[4-(4-methylpyridin-2-ylamino)butyrylamino]acetylamino}-3-(4-naphthalen-2-ylphenyl)propionate;
with methyl 3-(2-aminoacetylamino)-3-(4'-fluoro-2'-hydroxybiphenyl-4-yl)propionate hydrochloride
  methyl 3-{2-[4-(4-methylpyridin-2-ylamino)butyrylamino]acetylamino}-3-(4'-fluoro-2'-hydroxybiphenyl-4-yl)propionate;
with methyl 3-(2-aminoacetylamino)-3-(2-hydroxybiphenyl-4-yl)propionate hydrochloride
  methyl 3-{2-[4-(4-methylpyridin-2-ylamino)butyrylamino]acetylamino}-3-(2-hydroxybiphenyl-4-yl)propionate;

EXAMPLE 23

Hydrolysis of the methyl esters of the compounds of Example 22 in analogy to Example 2 (4) results in
3-{2-[4-(4-methylpyridin-2-ylamino)butyrylamino]acetylamino}-3-(4-nitrophenyl)propionic acid,
3-{2-[4-(4-methylpyridin-2-ylamino)butyrylamino]acetylamino}-3-(4-nitrophenyl)propionic acid sodium salt,
3-{2-[4-(4-methylpyridin-2-ylamino)butyrylamino]acetylamino}-3-(4-nitrophenyl)propionic acid trifluoroacetate;

3-{2-[4-(4-methylpyridin-2-ylamino)butyrylamino]acetylamino}-3-(3-nitro-2-hydroxyphenyl)propionic acid,
3-{2-[4-(4-methylpyridin-2-ylamino)butyrylamino]acetylamino}-3-(3-nitro-2-hydroxyphenyl)propionic acid sodium salt,
3-{2-[4-(4-methylpyridin-2-ylamino)butyrylamino]acetylamino}-3-(3-nitro-2-hydroxyphenyl)propionic acid trifluoroacetate;

3-{2-[4-(4-methylpyridin-2-ylamino)butyrylamino]acetylamino}-3-(4-chloro-3-nitrophenyl)propionic acid,
3-{2-[4-(4-methylpyridin-2-ylamino)butyrylamino]acetylamino}-3-(4-chloro-3-nitrophenyl)propionic acid sodium salt,
3-{2-[4-(4-methylpyridin-2-ylamino)butyrylamino]acetylamino}-3-(4-chloro-3-nitrophenyl)propionic acid trifluoroacetate, RT 21.44 min, FAB-MS (M+H)$^+$ 478;

3-(4'-fluorobiphenyl-3-yl)-3-{2-[4-(4-methylpyridin-2-ylamino)butyrylamino]acetylamino}propionic acid,
3-(4'-fluorobiphenyl-3-yl)-3-{2-[4-(4-methylpyridin-2-ylamino)butyrylamino]acetylamino}propionic acid sodium salt,
3-(4'-fluorobiphenyl-3-yl)-3-{2-[4-(4-methylpyridin-2-ylamino)butyrylamino]acetylamino}propionic acid trifluoroacetate, RT 26.32 min, FAB-MS (M+H)$^+$ 493;

3-(4'-fluorobiphenyl-4-yl)-3-{2-[4-(4-methylpyridin-2-ylamino)butyrylamino]acetylamino}propionic acid,
3-(4'-fluorobiphenyl-4-yl)-3-{2-[4-(4-methylpyridin-2-ylamino)butyrylamino]acetylamino}propionic acid sodium salt,
3-(4'-fluorobiphenyl-4-yl)-3-{2-[4-(4-methylpyridin-2-ylamino)butyrylamino]acetylamino}propionic acid trifluoroacetate;

3-{2-[4-(4-methylpyridin-2-ylamino)butyrylamino]acetylamino}-3-(4-naphthalen-1-ylphenyl)propionic acid,
3-{2-[4-(4-methylpyridin-2-ylamino)butyrylamino]acetylamino}-3-(4-naphthalen-1-ylphenyl)propionic acid sodium salt,
3-{2-[4-(4-methylpyridin-2-ylamino)butyrylamino]acetylamino}-3-(4-naphthalen-1-ylphenyl)propionic acid trifluoroacetate, RT* 25.44 min, FAB-MS (M+H)$^+$ 525;

3-{2-[4-(4-methylpyridin-2-ylamino)butyrylamino]acetylamino}-3-(4-naphthalen-1-yl-2-hydroxyphenyl)propionic acid,
3-{2-[4-(4-methylpyridin-2-ylamino)butyrylamino]acetylamino}-3-(4-naphthalen-1-yl-2-hydroxyphenyl)propionic acid sodium salt,
3-{2-[4-(4-methylpyridin-2-ylamino)butyrylamino]acetylamino}-3-(4-naphthalen-1-yl-2-hydroxyphenyl)propionic acid trifluoroacetate;

3-{2-[4-(4-methylpyridin-2-ylamino)butyrylamino]
   acetylamino}-3-(5-bromo-2-hydroxy-3-nitrophenyl)
   propionic acid,
3-{2-[4-(4-methylpyridin-2-ylamino)butyrylamino]
   acetylamino}-3-(5-bromo-2-hydroxy-3-nitrophenyl)
   propionic acid sodium salt,
3-{2-[4-(4-methylpyridin-2-ylamino)butyrylamino]
   acetylamino}-3-(5-bromo-2-hydroxy-3-nitrophenyl)
   propionic acid trifluoroacetate;

3-{2-[4-(4-methylpyridin-2-ylamino)butyrylamino]
   acetylamino}-3-(4-naphthalen-2-ylphenyl)propionic
   acid,
3-{2-[4-(4-methylpyridin-2-ylamino)butyrylamino]
   acetylamino}-3-(4-naphthalen-2-ylphenyl)propionic acid
   sodium salt,
3-{2-[4-(4-methylpyridin-2-ylamino)butyrylamino]
   acetylamino}-3-(4-naphthalen-2-ylphenyl)propionic acid
   trifluoroacetate;

3-(4'-fluoro-2'-hydroxybiphenyl-4-yl)-3-{2-[4-(4-methylpyridin-2-ylamino)butyrylamino]
   acetylamino}propionic acid,
3-(4'-fluoro-2'-hydroxybiphenyl-4-yl)-3-{2-[4-(4-methylpyridin-2-ylamino)butyrylamino]
   acetylamino}propionic acid sodium salt,
3-(4'-fluoro-2'-hydroxybiphenyl-4-yl)-3-{2-[4-(4-methylpyridin-2-ylamino)butyrylamino]
   acetylamino}propionic acid trifluoroacetate;

3-(4'-fluoro-2'-hydroxybiphenyl-3-yl)-3-{2-[4-(4-methylpyridin-2-ylamino)butyrylamino]
   acetylamino}propionic acid,
3-(4'-fluoro-2'-hydroxybiphenyl-3-yl)-3-{2-[4-(4-methylpyridin-2-ylamino)butyrylamino]
   acetylamino}propionic acid sodium salt,
3-(4'-fluoro-2'-hydroxybiphenyl-3-yl)-3-{2-[4-(4-methylpyridin-2-ylamino)butyrylamino]
   acetylamino}propionic acid trifluoroacetate or 3-(2-hydroxybiphenyl-3-yl)-3-{2-[4-(4-methylpyridin-2-ylamino)butyrylamino]acetylamino}propionic acid,
3-(2-hydroxybiphenyl-3-yl)-3-{2-[4-(4-methylpyridin-2-ylamino)butyrylamino]acetylamino}propionic acid
   sodium salt,
3-(2-hydroxybiphenyl-3-yl)-3-{2-[4-(4-methylpyridin-2-ylamino)butyrylamino]acetylamino}propionic acid trifluoroacetate.

EXAMPLE 24

1. Hydrochlorides 1 mmol of 3-(3-nitrophenyl)-3-{2-[5-(4-methylpyridin-2-ylamino)pentanoylamino]acetylamino}propionic acid trifluoroacetate from Example 6 is dissolved in 10 ml of water, and 0.1% HCl solution is added dropwise. The solution is freeze dried. The procedure is repeated several times. 3-(3-nitrophenyl)-3-{2-[5-(4-methylpyridin-2-ylamino)pentanoylamino]acetylamino}propionic acid hydrochloride is obtained, RT* 17.53 min, FAB-MS (M+H)$^+$ 458.
Analogously,
3-{2-[4-(4-methylpyridin-2-ylamino)butyrylamino]acetylamino}-3-(3-nitrophenyl)propionic acid trifluoroacetate from Example 4 gives 3-{2-[4-(4-methylpyridin-2-ylamino)butyrylamino]acetylamino}-3-(3-nitrophenyl)propionic acid hydrochloride, RT 15.13 min, FAB-MS (M+H)$^+$ 444.

2. Zwitterions

The zwitterion may also precipitate, depending on the addition of sodium hydroxide solution in analogy to Example 2(4). The zwitterion corresponding to the compound 3-(3-nitrophenyl)-3-{2-[5-(4-methylpyridin-2-ylamino)pentanoylamino]acetylamino}propionic acid has the following analytical data: RT* 17.53 min, FAB-MS (M+H)$^+$ 458, m.p. 221–222°.

The zwitterion corresponding to the compound 3-{2-[4-(4-methylpyridin-2-ylamino)butyrylamino]acetylamino}-3-(3-nitrophenyl)propionic acid has the following analytical data: RT* 17.01 min, FAB-MS (M+H)$^+$ 444, m.p. 212–213°.

3. Methanesulfonates 1 mmol of 3-(3-nitrophenyl)-3-{2-[5-(4-methylpyridin-2-ylamino)pentanoylamino]acetylamino}propionic acid trifluoroacetate from Example 6 is dissolved in 10 ml of water, and methanesulfonic acid is added dropwise. The solution is freeze dried. 3-(3-nitrophenyl)-3-{2-[5-(4-methylpyridin-2-ylamino)pentanoylamino]acetylamino}propionic acid methanesulfonate is obtained.
Analogously,
3-{2-[4-(4-methylpyridin-2-ylamino)butyrylamino]acetylamino}-3-(3-nitrophenyl)propionic acid trifluoroacetate from Example 4 gives 3-{2-[4-(4-methylpyridin-2-ylamino)butyrylamino]acetylamino}-3-(3-nitrophenyl)propionic acid methanesulfonate, RT* 17.07 min, FAB-MS (M+H)$^+$ 444.

EXAMPLE 25

(1) 0.06 mmol of 3-nitrobenzaldehyde, 5.72 g of malonic acid, 8.5 g of ammonium acetate and 40 ml of ethanol are boiled under reflux for 8 hours and stirred at room temperature overnight. The cooled reaction mixture is then filtered with suction, washed with ethanol and ether and dried in air. 3-amino-3-(3-nitrophenyl)propionic acid is obtained. Subsequent N-acylation with phenylacetyl chloride under standard conditions produces 3-(3-nitrophenyl)-3-phenylacetylaminopropionic acid. This racemate is dissolved in 40 ml of water, and the solution is adjusted to pH 7.5 with potassium hydroxide. The enzyme penicillin amidase is added and shaken for 3 days. Removal of the enzyme by filtration and the usual workup result in (R)-3-amino-3-(3-nitrophenyl)propionic acid and (S)-3-(3-nitrophenyl)-3-phenylacetylaminopropionic acid.

(R)-3-amino-3-(3-nitrophenyl)propionic acid is esterified in analogy to Example 2 by activation with thionyl chloride and reaction with methanol under standard conditions to give methyl 3-amino-3-(3-nitrophenyl)propionate, which is reacted with BOC-Gly-OH and 4-(4-methylpyridin-2-ylamino)butyric acid. Cleavage of the ester results in (R)-3-{2-[4-(4-methylpyridin-2-ylamino)butyrylamino]acetylamino}-3-(3-nitrophenyl)propionic acid. Use of an excess of NaOH results in the sodium salt of (R)-3-{2-[4-(4-methylpyridin-2-ylamino)butyrylamino]acetylamino}-3-(3-nitrophenyl)propionic acid. Preparative HPLC results in (R)-3-{2-[4-(4-methylpyridin-2-ylamino)butyrylamino]acetylamino}-3-(3-nitrophenyl)propionic acid trifluoroacetate, RT* 16.89 min, FAB-MS (M+H)$^+$ 444.

(S)-3-(3-nitrophenyl)-3-phenylacetylaminopropionic acid is treated with 10 ml of 6N HCl solution. (S)-3-amino-3-(3-nitrophenyl)propionic acid is obtained and is reacted further in analogy to the R enantiomer. This gives (S)-3-{2-[4-(4-methylpyridin-2-ylamino)butyrylamino]acetylamino}-3-(3-nitrophenyl)propionic acid, (S)-3-{2-[4-(4-methylpyridin-2-ylamino)butyrylamino]acetylamino}-3-(3-nitrophenyl propionic acid sodium salt, (S)-3-{2-[4-(4-methylpyridin-2-ylamino)butyrylamino]acetylamino}-3-(3-nitrophenyl)propionic acid trifluoroacetate, RT* 16.89 min, FAB-MS (M+H)$^+$ 444.

EXAMPLE 26

Prodrugs

1. Esterification of 3-(4-chloro-3-nitrophenyl)-3-{2-[5-(4-methylpyridin-2-ylamino)pentanoylamino]acetylamino}propionic acid by activation with thionyl chloride and reaction with ethanol under standard conditions produces ethyl 3-(4-chloro-3-nitrophenyl)-3-{2-[5-(4-methylpyridin-2-ylamino)pentanoylamino]acetylamino}propionate hydrochloride, RT 27.95, FAB-MS (M+H)$^+$ 520.

The following are produced analogously by esterification and subsequent preparative HPLC of 3-(4-chloro-3-nitrophenyl)-3-{2-[4-(4-methylpyridin-2-ylamino)butyrylamino]acetylamino}propionic acid ethyl 3-(4-chloro-3-nitrophenyl)-3-{2-[4-(4-methylpyridin-2-ylamino)butyrylamino]acetylamino}propionate trifluoroacetate, RT 27.57, FAB-MS (M+H)$^+$ 506;

of 3-(4-chloro-3-nitrophenyl)-3-{2-[4-(pyridin-2-ylamino)butyrylamino]acetylamino}propionic acid ethyl 3-(4-chloro-3-nitrophenyl)-3-{2-[4-(pyridin-2-ylamino)butyrylamino]acetylamino}propionate trifluoroacetate, RT* 15.29, FAB-MS (M+H)$^+$ 492;

of (R)-3-(3-nitrophenyl)-3-{2-[4-(4-methylpyridin-2-ylamino)butyrylamino]acetylamino}propionic acid ethyl (R)-3-(3-nitrophenyl)-3-{2-[4-(4-methylpyridin-2-ylamino)butyrylamino]acetylamino}propionate trifluoroacetate, RT* 20.61, FAB-MS (M+H)$^+$ 472;

of (S)-3-(3-nitrophenyl)-3-{2-[4-(4-methylpyridin-2-ylamino)butyrylamino]acetylamino}propionic acid ethyl (S)-3-(3-nitrophenyl)-3-{2-[4-(4-methylpyridin-2-ylamino)butyrylamino]acetylamino}propionate trifluoroacetate, RT* 20.61, FAB-MS (M+H)$^+$ 472;

of 3-(4-chloro-3-nitrophenyl)-3-{2-[5-(4-methylpyridin-2-ylamino)pentanoylamino]acetylamino}propionic acid ethyl 3-(4-chloro-3-nitrophenyl)-3-{2-[5-(4-methylpyridin-2-ylamino)pentanoylamino]acetylamino}propionate hydrochloride, RT 27.95, FAB-MS (M+H)$^+$ 520 or of 3-(4'-fluorobiphenyl-3-yl)-3-{2-[5-(pyridin-2-ylamino)pentanoylamino]acetylamino}propionic acid ethyl 3-(4'-fluorobiphenyl-3-yl)-3-{2-[5-(pyridin-2-ylamino)pentanoylamino]acetylamino}propionate trifluoroacetate, RT 30.26, FAB-MS (M+H)$^+$ 521.

2. Esterification of 3-(3-nitrophenyl)-3-{2-[4-(4-methylpyridin-2-ylamino)butyrylamino]acetylamino}propionic acid by activation with thionyl chloride and reaction with tert-butanol under standard conditions produces after preparative HPLC tert-butyl 3-(3-nitrophenyl)-3-{2-[4-(4-methylpyridin-2-ylamino)butyrylamino]acetylamino}propionate trifluoroacetate, RT 27.20, FAB-MS (M+H)$^+$500.

Obtained analogously by esterification with propanol is propyl 3-(3-nitrophenyl)-3-{2-[4-(4-methylpyridin-2-yl-amino)butyrylamino]acetylamino}propionate trifluoro-acetate, RT* 22.24, FAB-MS (M+H)$^+$486;

with isopropanol is isopropyl 3-(3-nitrophenyl)-3-{2-[4-methylpyridin-2-ylamino)butyrylamino]acetylamino}propionate trifluoro-acetate, RT* 22.03, FAB-MS (M+H)$^+$486 or with butanol is butyl 3-(3-nitrophenyl)-3-{2-[4-(4-methylpyridin-2-yl-amino)butyrylamino]acetylamino}propionate trifluoro-acetate, RT* 24.00, FAB-MS (M+H)$^+$500.

3. Reaction of 3-(3-nitrophenyl)-3-{2-[4-(4-methylpyridin-2-ylamino)butyrylamino]acetylamino}propionic acid with chloromethyl 2,2-dimethylpropionate under standard conditions products after preparative HPLC 3-{2-[4-(4-methylpyridin-2-ylamino)butyrylamino]acetyl-amino}-3-(3-nitrophenyl)propionyloxymethyl 2,2-dimethylpropionate trifluoroacetate, RT 69.68, FAB-MS (M+H)$^+$ 558.

4. Reaction of 3-(3-nitrophenyl)-3-{2-[4-(4-methylpyridin-2-ylamino)butyrylamino]acetylamino}propionic acid with diethylene glycol under standard conditions produces after preparative HPLC glycol 3-{2-[4-(4-methylpyridin-2-ylamino)butyrylamino]acetylamino}-3-(3-nitrophenyl)propionate trifluoroacetate.

5. Reaction of 3-(3-nitrophenyl)-3-{2-[4-(4-methylpyridin-2-ylamino)butyrylamino]acetylamino}propionic acid with benzyl alcohol under standard conditions produces after preparative HPLC benzyl 3-{2-[4-(4-methylpyridin-2-ylamino)butyrylamino]acetylamino}-3-(3-nitrophenyl)propionate trifluoroacetate.

EXAMPLE 27

Assays

The angiogenic blood vessels of a tumour noticeably show αvβ3 integrin and can thus be traced specifically by αvβ3-specific inhibitors.

It has been possible with the aid of an analytical method to identify cell lines which were obtainable from human tumours and which present the integrin αvβ6 but not the integrin αvβ3, for example Detroit 562, HT-29 and UCLA-P3, or which present both integrins αvβ3 and αvβ6, for example Calu-3 and Capan-2. (Analytical method: immunoprecipitation and fluorescence-activated cell sorting analysis). These identified cell lines grow in immunocompromised rodents, for example in nu/nu mice, as subcutaneous tumours.

Inhibitors of the αvβ3 integrin receptor block tumour growth in the way already described, in that the blood vessels growing into the tumour are exposed to apoptotic signals and die due to programmed cell death (apoptosis) (lit: P. C. Brooks, Eur. J. Cancer 1996, 32A, 2423–2429. P. C. Brooks et al., Cell 1994, 79 1157–1164 or S. Stomblad et al., J. Clin, Invest 1996, 98, 426–433).

The αvβ6 integrin inhibitors directly impair tumour development. The synergistic effect of the combined therapy according to the invention is documented by the following series of tests analogous to the test systems of Mitjans et al., J. Cell. Sci. 1995, 108, 2825–2838: αvβ6-expressing tumour cells are implanted subcutaneously in, for example nu/nu mice. In analogy to the M21 cell line of Mitjans et al., the growth of these tumour cells in the mice is observed depending on the integrin inhibitors.

After implantation of the tumour cells, the mice prepared in this way are separated and divided into groups each of 10 mice. The mice are treated each day according to the invention with the appropriate integrin inhibitors by an intraperitoneal injection, and the growth of the tumours is observed. The control group receives injections of sterile pyrogen-free saline. The tumour size is measured twice a week, and the corresponding tumour volume is calculated.

The following examples relate to pharmaceutical compositions:

EXAMPLE 1

Vials

A solution of 100 g of an active ingredient of the formula I and 5 g of disodium hydrogen phosphate in 3 l of double-distilled water is adjusted to pH 6.5 with 2 N hydrochloric acid, sterilized by filtration, dispensed into vials, lyophilized under sterile conditions and sealed sterile. Each vial contains 5 mg of active ingredient.

EXAMPLE B

Suppositories

A mixture of 20 g of an active ingredient of the formula I with 100 g of soya lecithin and 1400 g of cocoa butter is melted, poured into moulds and left to cool. Each suppository contains 20 mg of active ingredient.

EXAMPLE C

Solution

A solution is prepared from 1 g of an active ingredient of the formula I, 9.38 g of $NaH_2PO_4.2H_2O$, 28.48 g of $Na_2HOP_4.12H_2O$ and 0.1 g of benzalkonium chloride in 940 ml of double-distilled water. The pH is adjusted to 6.8, the volume is made up to 1 l, and the solution is radiation-sterilized. This solution can be used in the form of eye drops.

EXAMPLE D

Ointment 500 mg of an active ingredient of the formula I are mixed with 99.5 g of petrolatum under aseptic conditions.

EXAMPLE E

Tablets

A mixture of 1 kg of active ingredient of the formula I, 4 kg of lactose, 1.2 kg of potato starch, 0.2 kg of talc and 0.1 kg of magnesium stearate is compressed to tablets in a conventional way so that each tablet contains 10 mg of active ingredient.

EXAMPLE F

Coated Tablets

Tablets are compressed in analogy to Example E and are then coated in a conventional way with a coating of sucrose, potato starch, talc, tragacanth and dye.

EXAMPLE G

Capsules 2 kg of active ingredient of the formula I are packed in a conventional way into hard gelatin capsules so that each capsule contains 20 mg of the active ingredient.

EXAMPLE H

Ampoules

A solution of 1 kg of active ingredient of the formula I in 60 l of double-distilled water is sterilized by filtration, dispensed into ampoules, lyophilized under sterile conditions and sealed sterile. Each ampoule contains 10 mg of active ingredient.

EXAMPLE I

Inhalation Spray 14 g of active ingredient of the formula I are dissolved in 10 l of isotonic NaCl solution, and the solution is dispensed into commercially available pump-actuated sprays. The solution can be sprayed into the mouth or nose. One puff (about 0.1 ml) corresponds to a dose of about 0.14 mg.

What is claimed is:

1. A compound of formula I

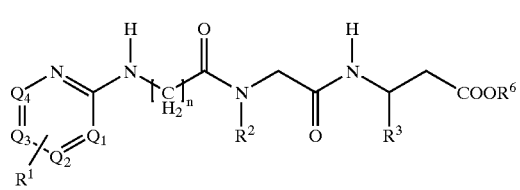

in which $Q_1$, $Q_2$, $Q_3$ or $Q_4$ is, in each case, independently of one another, CH or N, with the sum of N atoms in the ring being not more than 4, $R^1$ is H, A, Ar, Hal, OH, OA, $CF_3$ or $OCF_3$.

$R^2$ is H or A, $R^3$ is, 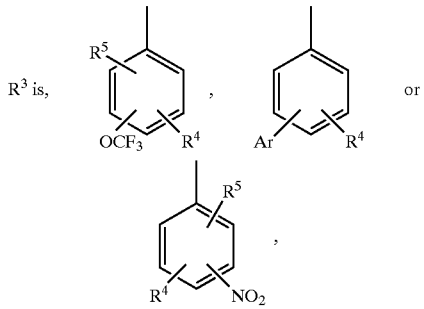

$R^4$ and $R^5$ are, in each case, independently of one another, H, A, Hal, OH, OA, $CF_3$, $OCF_3$, CN, $NH_2$, NHA, $NA_2$ or NH—C(O)A, $R^6$ is H, A, —$(CH_2)_m$—OH, —$(CH_2)_m$—O—C(O)A or —$(CH_2)_m$—Ar, A is alkyl with 1 or 6 C atoms, Ar is unsubstituted or mono-, di or trisubstituted aryl, Hal is F, Cl, Br or I, n is 2, 3, 4, 5 or 6 m is 1, 2, 3 or 4 or a physiologically acceptable salt or solvate thereof.

2. A compound according to claim 1, which is (a) 3-(4-methyl-3-nitrophenyl)-3-(2-[4-(pyridin-2-ylamino)butyrylamino]acetylamino)propionic acid, (b) 3-(4-methyl-3-nitrophenyl)-3-{2-[5-(pyridin-2-ylamino)pentanoylamino]acetylamino}propionic acid, (c) 3-(4-methyl-3-nitrophenyl)-3-{2-[5-(4-methyl-pyridin-2-ylamino)pentanoylamino]-acetylamino}propionic acid, (d) 3-(2-nitrophenyl)-3-{2-[5-(pyridin-2-yl-amino)pentanoylamino]acetylamino}propionic acid, (e) 3-{2-[4-(4-methylpyridin-2-ylamino)butyryl-amino]acetylamino}-3-(2-nitrophenyl)propionic acid, (f) 3-{2-[5-(4-methylpyridin-2-ylamino)pentanoyl-amino]acetylamino}-3-(2-nitrophenyl)propionic acid, (g) 3-{2-[4-(4-methylpyridin-2-ylamino)butyryl-amino]acetylamino}-3-(4-trifluoromethoxy-phenyl)propionic acid, (h) 3-{2-[5-(4-methylpyridin-2-ylamino)pentanoyl-amino]acetylamino}-3-(4-trifluoromethoxy-phenyl) propionic acid, (i) 3-{2-[5-(4-methylpyridin-2-ylamino)pentanoyl-amino]acetylamino}-3-(3-trifluoromethoxy-phenyl) propionic acid, (j) 3-{2-[4-(4-methylpyridin-2-ylamino)butyryl-amino]acetylamino}-3-(biphenyl-4-yl)propionic acid, (k) 3-(4-methyl-3-nitrophenyl)-3-{2-[5-(6-methyl-pyridin-2-ylamino)pentanoylamino]acetyl-amino}propionic acid, (l) 3-(4-chloro-3-nitrophenyl)-3-{2-[5-(4-methyl-pyridin-2-ylamino)pentanoylamino]acetyl-amino}propionic acid or (m) 3-(4-methyl-3-nitrophenyl)-3-{2-[5-(pyrimid-in-2-ylamino)pentanoylamino]acetylamino}propionic acid.

3. A compound of formula I

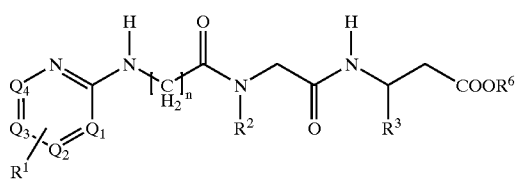

in which one of $Q_1$, $Q_2$, $Q_3$ or $Q_4$ is N, and the others are CH,

R1 is H, A, Ar, Hal, OH, OA, $CF_3$ or $OCF_3$, $R^2$ is H or A,

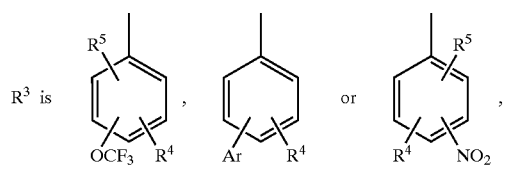

$R^4$ and $R^5$ are, in each case, independently of one another, H, A, Hal, OH, OA, $CF_3$, $OCF_3$, CN, $NH_2$, NHA, $NA_2$ or NH—C(O)A, $R^6$ is H, A, —$(CH_2)_m$—OH, —$(CH_2)_m$—O—C(O)A or —$(CH_2)_m$—Ar, A is alkyl with 1 to 6 C atoms, Ar is unsubstituted or mono-, di- or trisubstituted aryl, Hal is F, Cl, Br or I, n is 2, 3, 4, 5 or 6 m is 1, 2, 3, or 4 or a physiologically acceptable salt or solvate thereof.

4. A process for preparing a compound of formula I according to claim 1, or a salt or solvate thereof, comprising reacting:

(a) a compound of formula II

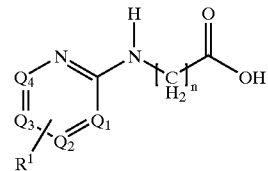

in which $Q_1$, $Q_2$, $Q_3$, $Q_4$, $R^1$ and n have the meanings stated in claim 1, with a compound of the formula III

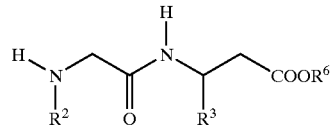

in which $R^2$, $R^3$, $R^4$, $R^5$ and $R^6$ have the meanings stated in claim 1, and optionally converting $R^{6 \neq H}$ into $R^6$=H, or (b) reacting a compound of formula IV

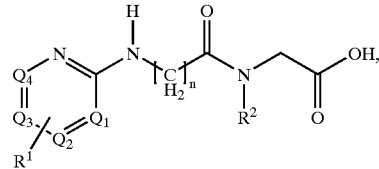

in which $Q_1$, $Q_2$, $Q_3$, $Q_4$, $R^1$, $R^2$ and n have the meanings stated in claim 1, with a compound of formula V

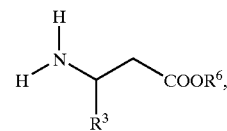

in which $R^3$, $R^4$, $R^5$ and $R^6$ have the meanings stated in claim 1, and optionally converting $R^6$=H, or (c) converting one or more radicals $R^1$, $R^2$, $R^3$, $R^4$ and/or $R^5$ in a compound of the formula I into one or more radicals $R^1$, $R^2$, $R^3$, $R^4$ and/or $R^5$ by vi) alkylating a hydroxyl group, vii) hydrolyzing an ester group to a carboxyl group, viii) esterifying a carboxyl group, ix) alkylating an amino group or x) acylating an amino group, and/or converting a basic or acidic compound of formula I by treatment with an acidic or base into a salt or solvate.

5. A pharmaceutical composition comprising at least one compound of formula I according to claim 1 or a physiologically acceptable salt or solvate thereof, and a pharmaceutically acceptable carrier.

6. A method of treating thromboses, myocardial infarct, coronary heart disease, arteriosclerosis, inflammations, tumours, osteoporosis, infections or restenosis after angioplasty, comprising administering a compound of formula I according to claim 1 or a physiologically acceptable salt or solvate thereof.

7. A method for treating pathological processes maintained or propagated by angiogenesis, comprising administering a compound of formula I according to claim 1 or a physiologically acceptable salt or solvate thereof.

8. A method as to claim 6, wherein the compounds of formula I is:
   a) 3-{2-[5-(4-methylpyridin-2-ylamino)pentanoyl-amino]acetylamino}-3-(4-chloro-3-nitrophenyl)-propionic acid trifluoroacetate;
   b) 3-(4-methyl-3-nitrophenyl)-3-{2-[5-(4--methyl-pyridin-2-ylamino)pentanoylamino]acetylamino}-propionic acid trifluoroacetate;
   c) 3-(4-methyl-3-nitrophenyl)-3-{2-[4-(pyridin-2-ylamino)butyrylamino]acetylamino}propionic acid trifluoroacetate;
   d) 3-{2-[5-(4-methylpyridin-2-ylamino)pentanoyl-amino]acetylamino}-3-(4-trifluoromethoxyphenyl)-propionic acid trifluoroacetate;
   e) 3-(biphenyl-4-yl)3-{2-[5-(pyridin-2-ylamino)-pentanoylamino]acetylamino}propionic acid trifluoroacetate;
   f) 3-{2-[4-(4-methylpyridin-2-ylamino)butyryl-amino]acetylamino}-3-(3-trifluoromethoxyphenyl)-propionic acid trifluoroacetate;
   g) 3-(3-nitrophenyl)-3-{2-[5-(4-methylpyridin-2-ylamino)pentanoylamino]acetylamino}propionic acid trifluoroacetate;
   h) 3-{2-[4-(4-methylpyridin-2-ylamino)butyryl-amino]acetylamino}-3-(4-methyl-3-nitrophenyl)-propionic acid trifluoroacetate;
   i) 3-(3-nitrophenyl)-3-{2-[4-(4-methylpyridin-2-ylamino)butyrylamino]acetylamino}propionic acid trifluoroacetate;
   j) 3-{2-[4-(4-methylpyridin-2-ylamino(butyryl-amino]acetylamino}-3-(4-trifluoromethoxyphenyl)-propionic acid trifluoroacetate;
   k) 3-{2-[5-(4-methylpyridin-2-ylamino)pentanoyl-amino]acetylamino}-3-(3-trifluoromethoxyphenyl)-propionic acid trifluoroacetate or
   l) 3-(3-nitrophenyl)-3-{2-[5-(4-methylpyridin-2-ylamino) pentanoylamino]acetylamino}propionic acid hydrochloride.

9. A method of treating tumors, comprising administering:
   a) 3-{2-[5-(4-methylpyridin-2-ylamino)pentanoyl-amino]acetylamino}-3-(4-chloro-3-nitrophenyl)-propionic acid trifluoroacetate;
   b) 3-(4-methyl-3-nitrophenyl)-3-{2-[5-(4-methyl-pyridin-2-ylamino)pentanoylamino]acetylamino}-propionic acid trifluoroacetate;
   c) 3-(4-methyl-3-nitrophenyl)-3-{2-[4-(pyridin-2-ylamino)butyrylamino]acetylamino}propionic acid trifluoroacetate;
   d) 3-{2-[5-(4-methylpyridin-2-ylamino)pentanoyl-amino]acetylamino}-3-(4-trifluoromethoxyphenyl)-propionic acid trifluoroacetate;
   e) 3-(biphenyl-4-yl)-3-{2-[5-(pyridin-2-ylamino)-pentanoylamino]acetylamino}propionic acid trifluoroacetate;
   f) 3-{2-[4-(4-methylpyridin-2-ylamino)butyryl-amino]acetylamino}-3-(3-trifluoromethoxyphenyl)-propionic acid trifluoroacetate;
   g) 3-(3-nitrophenyl)-3-{2-[5-(4-methylpyridin-2-ylamino)pentanoylamino]acetylamino}propionic acid trifluoroacetate;
   h) 3-{2-[4-(4-methylpyridin-2-ylamino)butyryl-amino]acetylamino}-3-(4-methyl-3-nitrophenyl)-propionic acid trifluoroacetate;
   i) 3-(3-nitrophenyl)-3-{2-[4-(4-methylpyridin-2-ylamino)butyrylamino]acetylamino}propionic acid trifluoroacetate;
   j) 3-{2-[4-(4-methylpyridin-2-ylamino)butyryl-amino]acetylamino}-3-(4-trifluoromethoxyphenyl)-propionic acid trifluoroacetate;
   k) 3-{2-[5-(4-methylpyridin-2-ylamino)pentanoyl-amino]acetylamino}-3-(3-trifluoromethoxyphenyl)-propionic acid trifluoroacetate or
   l) 3-(3-nitrophenyl)-3-{2-[5-(4-methylpyridin-2-ylamino) pentanoylamino]acetylamino}propionic acid hydrochloride, thereby suppressing angiogenesis of blood vessels growth into a tumour by inhibiting αvβ3 integrin receptors or αvβ5 integrin receptors, and/or inhibiting tumour development through inhibition of αvβ6 integrin receptor.

10. A method of treating metastases of solid tumours, angiofibromatosis, retrollental fibroplasias, haemangioma or Kaposi's sarcoma, comprising administering:
   a) 3-{2-[5-(4-methylpyridin-2-ylamino)pentanoyl-amino]acetylamino}-3-(4-chloro-3-nitrophenyl)-propionic acid trifluoroacetate;
   b) 3-(4-methyl-3-nitrophenyl)-3-{2-[5-(4-methyl-pyridin-2-ylamino)pentanoylamino]acetylamino}-propionic acid trifluoroacetate;
   c) 3-(4-methyl-3-nitrophenyl)-3-{2-[4-(pyridin-2-ylamino)butyrylamino]acetylamino}propionic acid trifluoroacetate;
   d) 3-{2-[5-(4-methylpyridin-2-ylamino)pentanoyl-amino]acetylamino}-3-(4-trifluoromethoxyphenyl)-propionic acid trifluoroacetate;
   e) 3(biphenyl-4-yl)-3-{2-[5-(pyridin-2-ylamino)-pentanoylamino]acetylamino}propionic acid trifluoroacetate;
   f) 3-{2-[4-(4-methylpyridin-2-ylamino)butyryl-amino]acetylamino}-3-(3-trifluoromethoxyphenyl)-propionic acid trifluoroacetate;
   g) 3-(3-nitrophenyl)-3-{2-[5-(4-methylpyridin-2-ylamino)pentanoylamino]acetylamino}propionic acid trifluoroacetate;
   h) 3-{2-[4-(4-methylpyridin-2-ylamino)butyryl-amino]acetylamino}-3-(4-methyl-3-nitrophenyl)-propionic acid trifluoroacetate;
   i) 3-(3-nitrophenyl)-3-{2-[4-(4-methylpyridin-2-ylamino)butyrylamino]acetylamino}propionic acid trifluoroacetate;
   j) 3-{2-[4-(4-methylpyridin-2-ylamino)butyryl-amino]acetylamino}-3-(4-trifluoromethoxyphenyl)-propionic acid trifluoroacetate;
   k) 3-{2-[5-(4-methylpyridin-2-ylamino)pentanoyl-amino]acetylamino}-3-(3-trifluoromethoxyphenyl)-propionic acid trifluoroacetate or
   l) 3-(3-nitrophenyl)-3-{2-[5-(4-methylpyridin-2-ylamino) pentanoylamino]acetylamino}propionic acid hydrochloride.

* * * * *

UNITED STATES PATENT AND TRADEMARK OFFICE
CERTIFICATE OF CORRECTION

| | | |
|---|---|---|
| PATENT NO. | : 6,576,637 B1 | Page 1 of 1 |
| APPLICATION NO. | : 09/913933 | |
| DATED | : June 10, 2003 | |
| INVENTOR(S) | : Guenter Hoelzemann et al. | |

It is certified that error appears in the above-identified patent and that said Letters Patent is hereby corrected as shown below:

Column 46, line 20, reads "growth" should read -- growing --

Signed and Sealed this

Twelfth Day of September, 2006

JON W. DUDAS
*Director of the United States Patent and Trademark Office*